United States Patent
Zlokarnik et al.

(10) Patent No.: US 6,200,762 B1
(45) Date of Patent: Mar. 13, 2001

(54) PHOTON REDUCING AGENTS AND COMPOSITIONS FOR FLUORESCENCE ASSAYS

(75) Inventors: Gregor Zlokarnik, San Diego; Paul Negulescu, Solana Beach; Tom Knapp, Encinitas; Roger Y. Tsien; Tim Rink, both of La Jolla, all of CA (US)

(73) Assignee: Aurora Biosciences Corporation, San Diego, CA (US)

( * ) Notice: Subject to any disclaimer, the term of this patent is extended or adjusted under 35 U.S.C. 154(b) by 0 days.

(21) Appl. No.: 09/118,497

(22) Filed: Jul. 17, 1998

Related U.S. Application Data

(60) Provisional application No. 60/054,519, filed on Aug. 1, 1997.

(51) Int. Cl.[7] .................... C12Q 1/70; C12Q 1/02; C12Q 1/34; G01N 33/542; B01L 3/00
(52) U.S. Cl. .................. 435/7.1; 435/5; 435/6; 435/7.1; 435/7.2; 435/7.24; 435/7.21; 435/7.5; 435/7.72; 435/91.1; 435/230; 435/235; 436/501; 436/528; 436/529; 436/530; 436/531; 436/546; 436/800; 436/809; 427/102; 427/157; 427/213.34; 422/82.05; 422/99
(58) Field of Search ................. 435/5, 6, 7.1, 7.2, 435/7.5, 7.21, 7.72, 7.92, 91.1, 230, 235; 436/501, 529, 531, 800, 528, 530, 546, 809; 427/102, 213.34, 157; 422/82.05, 99

(56) References Cited

U.S. PATENT DOCUMENTS

| | | |
|---|---|---|
| 4,192,917 | 3/1980 | Zurawski . |
| 4,658,020 | 4/1987 | Kung et al. . |
| 4,680,275 | 7/1987 | Wagner et al. . |

(List continued on next page.)

FOREIGN PATENT DOCUMENTS

| | | |
|---|---|---|
| 0 157 197 | 10/1985 | (EP) . |
| 270206 A1 | 8/1987 | (EP) . |
| 973040 | 7/1999 | (EP) . |

(List continued on next page.)

OTHER PUBLICATIONS

Benjouad et al., Fed. Europ. Biochem. Soc. 319:119–124 (1993).
Birkelund et al., Infect. Immun. 57:2683–2690 (1989).
Blach et al., Gamete Res. 21:233–241 (1988).
Bourinbaiar et al., J. Virol. Meth. 35:49–58 (1991).
Carmagnola et al., Clin. Exp. Immunol. 51:173–177 (1983).

(List continued on next page.)

Primary Examiner—Long V. Le
Assistant Examiner—Gailene R. Gabel
(74) Attorney, Agent, or Firm—Gray Cary Ware & Freidenrich LLP; Lisa A. Haile

(57) ABSTRACT

The present invention provides a method for reducing undesirable light emission from a sample using at least one photon producing agent and at least one photon reducing agent (e.g. dye-based photon reducing agents). The present invention further provides a method for reducing undesirable light emission from a sample (e.g., a biochemical or cellular sample) with at least one photon producing agent and at least one collisional quencher. The present invention also provides a method for reducing undesirable light emission from a sample (e.g., a biochemical or cellular sample) with at least one photon producing agent and at least one quencher, such as an electronic quencher. The present invention further provides a method of determining bound and free analyte in a sample using at least one photon reducing agent. The present invention also provides a method of screening test chemicals in fluorescent assays using photon reducing agents. The present invention also provides compositions and kits for practicing these methods.

48 Claims, 16 Drawing Sheets

U.S. PATENT DOCUMENTS

| | | |
|---|---|---|
| 4,758,523 | 7/1988 | Harjunmaa . |
| 4,770,992 | 9/1988 | Van den Engh et al. . |
| 4,800,159 | 1/1989 | Mullis et al. . |
| 4,837,162 | 6/1989 | Rothman et al. . |
| 4,863,875 | 9/1989 | Bailey et al. . |
| 4,954,435 | 9/1990 | Krauth . |
| 4,968,601 | 11/1990 | Jacobson et al. . |
| 4,977,077 | 12/1990 | Ngo et al. . |
| 4,994,373 | 2/1991 | Stavrianopoulos et al. . |
| 5,017,473 | 5/1991 | Wagner . |
| 5,032,381 | 7/1991 | Bronstein et al. . |
| 5,073,497 | 12/1991 | Schwartz . |
| 5,106,730 | 4/1992 | Van Ness et al. . |
| 5,118,602 | 6/1992 | Pendersen et al. . |
| 5,130,238 | 7/1992 | Malek et al. . |
| 5,177,073 | 1/1993 | Gulliya et al. . |
| 5,198,340 | 3/1993 | Mukku . |
| 5,210,412 | 5/1993 | Levis et al. . |
| 5,215,971 | 6/1993 | Datema et al. . |
| 5,294,799 | 3/1994 | Aslund et al. . |
| 5,424,414 | 6/1995 | Mattingly . |
| 5,434,088 | 7/1995 | Ikeda et al. . |
| 5,582,982 | 12/1996 | Cubbage et al. . |
| 5,616,505 | 4/1997 | Mattingly . |
| 5,625,048 | 4/1997 | Tsien et al. . |
| 5,627,074 | 5/1997 | Mathis et al. . |
| 5,628,310 * | 5/1997 | Rao et al. ............................ 128/632 |
| 5,661,035 | 8/1997 | Tsien et al. . |
| 5,670,113 | 9/1997 | Akong et al. . |
| 5,741,657 * | 4/1998 | Tsien et al. ............................ 435/18 |
| 5,763,189 * | 6/1998 | Buechler et al. ..................... 435/7.1 |
| 5,777,079 | 7/1998 | Tsien et al. . |
| 5,910,287 * | 6/1999 | Cassin et al. ......................... 422/102 |
| 5,928,869 * | 7/1999 | Nadeau et al. ............................ 435/6 |
| 5,928,888 * | 7/1999 | Whitney et al. ........................ 435/29 |

FOREIGN PATENT DOCUMENTS

| | | |
|---|---|---|
| WO 90/10715 | 9/1990 | (WO) . |
| 9313423 | 7/1993 | (WO) . |
| WO 96/23810 | 8/1996 | (WO) . |
| WO 96/30540 | 10/1996 | (WO) . |
| WO 96/41166 | 12/1996 | (WO) . |
| WO 97/28261 | 8/1997 | (WO) . |
| WO 98/13353 | 4/1998 | (WO) . |
| 9855231 | 12/1998 | (WO) . |
| 9942608 | 8/1999 | (WO) . |

OTHER PUBLICATIONS

Hemmila et al., Analyt. Biochem. 137:335–343 (1984).
Kan et al., Exp. Gerentol. 26:365–374 (1991).
Lakowicz, Principles of Fluorescence Spectroscopy, Plenum Press, New York, pp. 257–309.
Lawrence et al., Proc. Natl. Acad. Sci. U.S.A. 87:5420–5424 (1990).
Lin et al., Arteriosclerosis 10:703–709 (1990).
Louis et al., Neurosci. Letters pp. 257–260 (1989).
Lundemose et al., APMIS 97:68–74 (1989).
Lynch et al., Can. J. Vet. Res. 50:384–389 (1986).
Moreira et al., Virchows Archiv. A. Pathological Anatomy and Histopathology, 415:391–393 (1989).
Schloter et al., Soil. Biol. Biochem. 24:399–403 (1992).
Schols et al., J. Acquired Immune Deficiency Syndromes 2:10–15 (1989).
Schols et al., J. Gen. Virol. 70:2397–2408 (1989).
Soini and Hemmila, Clin. Chem. 25:353–361 (1979).
Spadoro et al., BioTechniques 8:186–193 (1990).
Yourno et al., J. Clin. Microbiol. 30:2887–2892 (1992).

* cited by examiner

—●— Intensities observed with 20x objective
—○— Calculated intensities (absorption only)

US 6,200,762 B1

PHOTON REDUCING AGENTS AND COMPOSITIONS FOR FLUORESCENCE ASSAYS

This application claims the benefit of priority under 35 U.S.C. §119(e) to United States provisional application No. 60/054,519, filed Aug. 1, 1997 now abandoned.

TECHNICAL FIELD

The present invention generally relates to methods and compositions for reducing undesired light from an assay sample, particularly fluorescence assays in living cells.

BACKGROUND

Cell-based assays are commonly used for drug discovery to screen large numbers of test chemicals for potential therapeutic activity. Typically, the cells contain a target, such as a protein. Test-chemicals, such as candidate ligands for a target protein, are screened for modulating activity of a target. Screening relies on a detectable change in a property of a cell that faithfully reports target activity in the presence of a test chemical. Many assays use optical methods to detect such activities. Fluorescence detection methods are particularly powerful tools in this regard, because fluorescence detection methods can be sensitive. Many different types of fluorescent probes are available for such assays, including fluorescent probes that act as enzyme substrates, labels for proteins and nucleic acids, indicators of intracellular ions, and sensors of membrane voltage.

Despite the recent plethora in available fluorescent tools for assays, fluorescence based assays can be plagued by undesirable, and sometimes intolerable, levels of background fluorescence. For example, solution fluorescence may increase the background fluorescence of the assay sample. Solution fluorescence can obscure a desired signal associated with a fluorescent probe. Solution fluorescence can arise from many sources, including fluorescent probe degradation, targets, cells, various solution components, and test chemicals.

In cell-based assays recently developed by one of the inventors of the present invention, solution fluorescence can give rise to lower signal to noise ratios. These cell-based assays utilize a membrane permeable substrate specific for beta-lactamase, a bacterial enzyme that is not normally expressed in mammalian cells. The substrate diffuses into the cell and is trapped inside the cell by the action of intracellular esterases. If a cell expresses a beta-lactamase reporter gene, the expressed enzyme will cleave the substrate. Before cleavage the substrate fluoresces green and after cleavage the substrate fluoresces blue. When such assays are used for high-throughput screening, increasing the signal to noise ratio can be advantageous because it increases the sensitivity of the screening system and reliability of the data. Solution fluorescence, however, often thwarts achieving advantageous signal to noise ratios. Solution fluorescence from test chemicals, substrate in the solution, and other solution components that bath the cells contribute to background fluorescence.

The present inventors recognized that membrane compartment assays, such as cell-based assays, that use optical methods could be improved by reducing unwanted light emitted from the solution bathing the membrane compartments, particularly solution fluorescence. The present inventors investigated different washing and incubation methods in an attempt to increase dye loading and retention while reducing solution fluorescence. Although the inventors could reduce solution fluorescence, such manipulations were cumbersome and time consuming.

Consequently, the present inventors developed compositions and methods for reducing the emission undesired light from solutions in membrane compartment assays that did not solely rely on washing or incubation methods. Such compositions and methods are much more applicable to high-throughput screening than improvements to washing and incubation methods.

SUMMARY

Figure 1A:
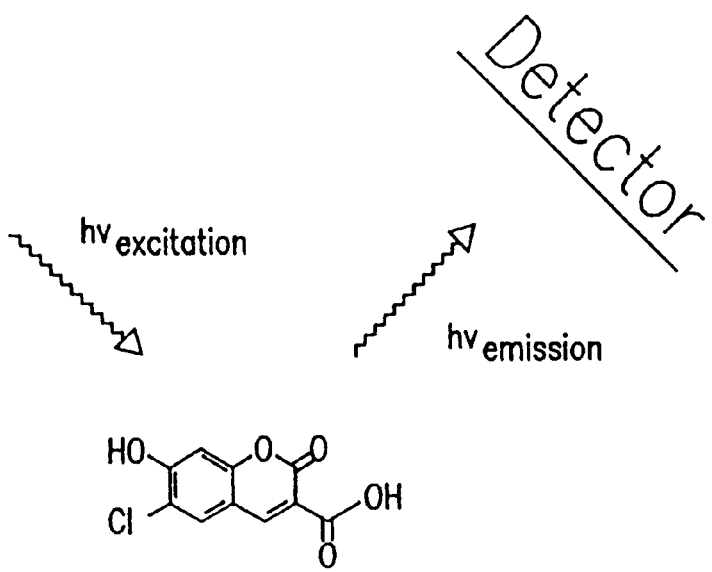
FIG. 1A is a diagram of fluorescence emission from a solution without a photon reducing agent.
Figure 1B:
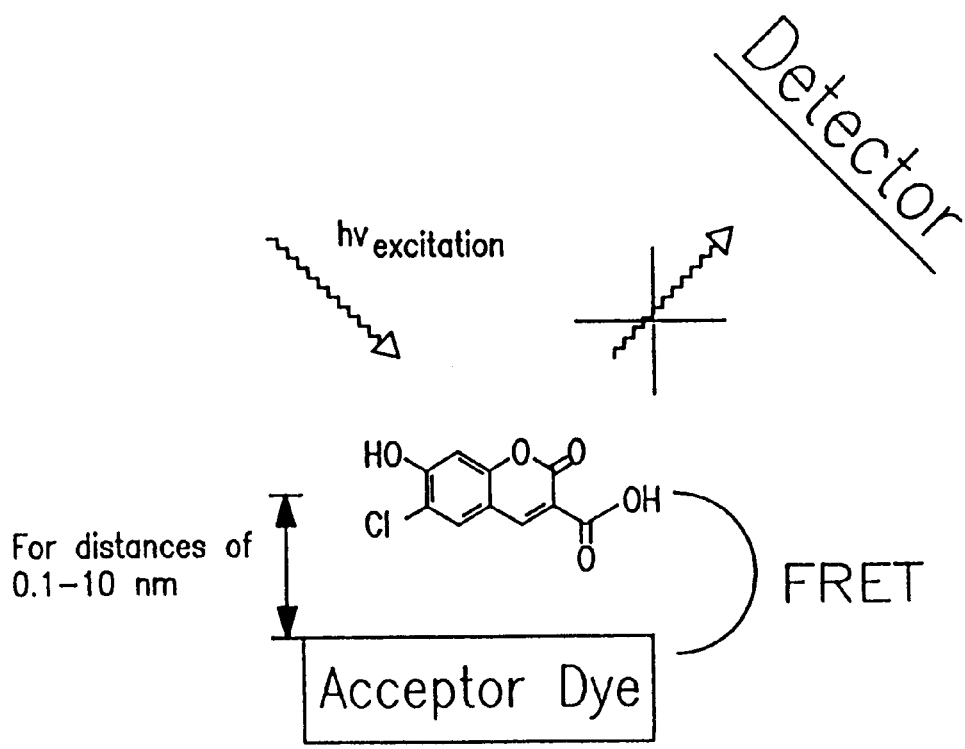
FIG. 1B is a diagram of fluorescence emission from a solution with a photon reducing agent.

The present invention provides for a method of reducing light emission, such as undesirable light, from a sample, such as a solution. The method can be used with fluorescent assays that are often hampered by solution fluorescence that interferes with detecting a desired signal from the sample. Membrane compartment based assays, such as cell-based assays, typically exhibit undesirable background fluorescence from probes, test chemicals, or other solution components that can interfere with desired signal detection. To overcome these problems, the inventors devised a method to reduce undesired light emitted from the sample by adding a photon reducing agent to the sample. These methods can be used, for example, to detect bound and free analyte in an analyte/anti-analyte reaction, to identify a chemical with a biological activity. The present invention also includes a therapeutic composition identified by such methods and a system to perform such methods and to identify a chemical with a toxicological or bioavailability activity.

The present invention also provides a composition of matter comprising a membrane compartment that is in physical or optical contact with a solid surface, such as a surface that can transmit light, and an aqueous solution with at least one photon reducing agent. The solid surface can be, for example, a well of a multi-well platform, such as a microtiter plate. Optionally, the membrane compartment need not be in contact with a solid surface. In this aspect of the present invention, the membrane compartment can be within a drop or droplet such as they are generated during FACS procedures.

The present invention also includes methods of determining bound and free analyte, such as in a specific binding reaction, wherein one member of an analyte/anti-analyte pair bound to a solid surface. Preferably, one member of an analyte/anti-analyte pair is a membrane compartment.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein, and the laboratory procedures in spectroscopy, drug discovery, cell culture, and molecular genetics, described below, are those well known and commonly employed in the art. Standard techniques are typically used for signal detection, recombinant nucleic acid methods, polynucleotide synthesis, and microbial culture and transformation (e.g., electroporation, and lipofection). The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y.; and Lakowicz, J. R. Principles of Fluorescence Spectroscopy, New York: Plenum Press (1983)) for fluorescence techniques, each of which are incorporated herein by reference) which are provided throughout this document. Standard techniques are used for chemical syntheses, chemical analyses, and biological assays. As employed throughout the disclosure, the following terms, unless otherwise indicated, shall be understood to have the following meanings:

"Fluorescent donor moiety" refers to the radical of a fluorescent compound that can absorb energy and is capable of transferring the energy to an acceptor, such as another fluorescent compound or another part of the fluorescent compound. Suitable donor fluorescent compounds include, but are not limited to, coumarins and related dyes, xanthene dyes such as fluoresceins, rhodols, and rhodamines, resorufins, cyanine dyes, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, and fluorescent europium and terbium complexes and related compounds.

"Quencher" refers to a molecule or part of a compound that is capable of reducing the emission from a fluorescent moiety. Such reduction includes reducing the light after the time when a photon is normally emitted from a fluorescent moiety. Quenching may occur by any of several mechanisms, including fluorescence resonance energy transfer, photoinduced electron transfer, paramagnetic enhancement of intersystem crossing, Dexter exchange coupling, and excitation coupling, such as the formation of dark complexes.

"Acceptor" refers to a quencher that operates via energy transfer. Acceptors may re-emit the transferred energy as fluorescence. Examples of acceptors include coumarins and related fluorophores, xanthenes such as fluoresceins, rhodols, and rhodamines, resorufins, cyanines, difluoroboradiazaindacenes, and phthalocyanines. Other chemical classes of acceptors generally do not re-emit the transferred energy. Examples include indigos, benzoquinones, anthraquinones, azo compounds, nitro compounds, indoanilines, and di- and triphenylmethanes.

"Binding pair" refers to two moieties (e.g. chemical or biochemical) that have an affinity for one another. Examples of binding pairs include antigen/antibodies, lectin/avidin, target polynucleotide/probe oligonucleotide, antibody/anti-antibody, receptor/ligand, enzyme/ligand and the like. "One member of a binding pair" refers to one moiety of the pair, such as an antigen or ligand.

"Dye" refers to a molecule or part of a compound that absorbs frequencies of light, including, but not limited to, ultraviolet light. The terms "dye" and "chromophore" are synonymous.

"Fluorophore" refers to a chromophore that fluoresces.

"Membrane-permeant derivative" refers to a chemical derivative of a compound that has enhanced membrane permeability compared to an underivativized compound. Examples include ester, ether and carbamate derivatives. These derivatives are made better able to cross cell membranes (i.e. membrane permeant) because hydrophilic groups are masked to provide more hydrophobic derivatives. Also, masking groups are designed to be cleaved from a precursor (e.g., fluorogenic substrate precursor) within a cell to generate the derived substrate intracellularly. Because the substrate is more hydrophilic than the membrane permeant derivative, it becomes trapped within the cell. Membrane-permeant and membrane-impermeant are relative terms based on the permeability characteristics of a compound and a chemical derivative thereof.

"Isolated polynucleotide" refers a polynucleotide of genomic, cDNA, or synthetic origin, or some combination there of, which by virtue of its origin the "isolated polynucleotide" (1) is not associated with the cell in which the "isolated polynucleotide" is found in nature, or (2) is operably linked to a polynucleotide which it is not linked to in nature.

"Isolated protein" refers a protein, encoded by cDNA, recombinant RNA, or synthetic nucleic acids, or some combination thereof, which by virtue of its origin the "isolated protein" (1) is not associated with proteins that it is normally found with in nature, (2) is isolated from the cell in which it normally occurs, (3) is isolated free of other proteins from the same cellular source (e.g. free of human proteins), (4) is expressed by a cell from a different species, or (5) does not occur in nature. "Isolated naturally occurring protein" refers to a protein which by virtue of its origin the "isolated naturally occurring protein" (1) is not associated with proteins that it is normally found with in nature, or (2) is isolated from the cell in which it normally occurs, or (3) is isolated free of other proteins from the same cellular source, e.g. free of human proteins.

"Polypeptide" as used herein as a generic term to refer to native protein, fragments, or analogs of a polypeptide sequence. Hence, native protein, fragments, and analogs are species of the polypeptide genus.

"Naturally-occurring" as used herein, as applied to an object, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Operably linked" refers to a juxtaposition wherein the components so described are in a relationship permitting them to function in their intended manner. For example, a control sequence "operably linked" to a coding sequence is linked (for example, ligated) in such a way that expression of the coding sequence is achieved under conditions compatible with the control sequences, such as when the appropriate molecules (e.g., inducers and polymerases) are bound to the control or regulatory sequence(s).

"Control sequence" refers to polynucleotide sequences that are necessary to effect the expression of coding and non-coding sequences to which they are linked (for example, ligated). The nature of such control sequences differs depending upon the host organism. In eukaryotes, such control sequences generally include enhancers, promoters, ribosomal binding sites, and transcription termination sequences. In prokaryotes, generally, such control sequences include promoters and transcription termination sequence. The term "control sequences" is intended to include, at a minimum, components whose presence can influence the expression of a gene, and can include additional components whose presence is advantageous, for example, leader sequences and fusion partner sequences (for example, sequences encoding a fusion protein).

"Polynucleotide" refers to a polymeric form of nucleotides of at least 10 bases in length, either ribonucleotides or deoxynucleotides or a modified form of either type of nucleotide. The term includes single and double stranded forms of DNA.

"Corresponds to" refers to a sequence that is homologous (i.e., is identical, not strictly evolutionarily related) to all or a portion of a reference sequence.

"Membrane compartment" refers to a semi-permeable material (for example, a biological membrane, vesicle, cell (for example, prokaryotic or eukaryotic, such as mammalian, such as human), liposome, envelope of a virus, or the like, surrounding a volume of aqueous fluid, such as intracellular fluid.

"Modulation" refers to the capacity to either enhance or inhibit a functional property of biological activity or process (e.g., enzyme activity or receptor binding). Such enhancement or inhibition may be contingent upon the occurrence of a specific event, such as activation of a signal transduction pathway, and can be exhibited only in particular cell types.

The term "modulator" refers to a chemical compound (naturally occurring or non-naturally occurring), such as a biological macromolecule (e.g., nucleic acid, protein, non-peptide, or organic molecule), or an extract made from biological materials such as bacteria, plants, fungi, or animal (particularly mammalian, including human) cells or tissues. Modulators are evaluated for potential activity as inhibitors or activators (directly or indirectly) of a biological process or processes (e.g., agonist, partial antagonist, partial agonist, inverse agonist, antagonist, antineoplastic agents, cytotoxic agents, inhibitors of neoplastic transformation or cell proliferation, cell proliferation-promoting agents, and the like) by inclusion in screening assays described herein. The activity of a modulator may be known, unknown or partially known.

The term "test chemical" refers to a chemical to be tested by one or more screening method(s) of the invention as a putative modulator. A test chemical can be any chemical, such as an inorganic chemical, an organic chemical, a protein, a peptide, a carbohydrate, a lipid, or a combination thereof.

The terms "label" or "labeled" refers to incorporation of a detectable marker. For example, by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^{3}$H, $^{14}$C, $^{35}$S, $^{125}$I, $^{131}$I ), fluorescent labels (e.g., FITC, rhodamine, lanthanide phosphors), enzymatic labels or a product of a reporter gene (e.g., horseradish peroxidase, beta-galactosidase, beta-latamase, luciferase, and alkaline phosphatase), other labels such as chemiluminescent labels, biotinyl groups, or predetermined polypeptide epitopes recognized by a secondary reporter (e.g., leucine zipper pair sequences, binding sites for secondary antibodies, metal binding domains, and epitope tags). In some embodiments, labels are attached by spacer arms of various lengths to reduce potential steric hindrance.

"Fluorescent label" refers to a fluorescent moiety incorporated onto or within a chemical structure having desirable properties, such as binding with a target or attaching to a polypeptide of biotinyl moieties that can be detected by avidin (e.g., streptavidin containing a fluorescent label or enzymatic activity that can be detected by fluorescence detection methods). Various methods of fluorescently labeling polypeptides, glycoproteins and other moieties are known in the art and may be used. Examples of labels for polypeptides include, but are not limited to dyes (e.g., FITC and rhodamine), intrinsically fluorescent proteins, and lanthanide phosphors. In some embodiments, labels are attached by spacer arms of various lengths to reduce potential steric hindrance.

"Photon reducing agent" refers to a molecule or particle, such as a colloidal particle, that reduces that amount of light emitted from another molecule in a sample or reduces the amount of light that excites another molecule in a sample. Typically, a photon reducing agent reduces the amount of light emitted from another molecule in a sample by having an absorption spectrum that overlaps with the absorption, excitation, or emission spectrum of a molecule that produces photons. Alternatively, some photon reducing agents may engage in energy transfer (e.g., fluorescence resonance energy transfer (FRET)) with a photon producing agent that prevents or alters the emission of light from the photon producing agent.

"Photon producing agent" refers to a molecule that can emit photons. Typically, a photon producing agent produces photons by absorbing light at one wavelength and emitting light of another wavelength.

"Reporter gene" refers to a nucleotide sequence encoding a protein that is readily detectable either by its presence or activity, including, but not limited to, luciferase, green fluorescent protein, chloramphenicol acetyl transferase, beta-galactosidase, secreted placental alkaline phosphatase, beta-lactamase, human growth hormone, and other secreted enzyme reporters. Generally, reporter genes encode a polypeptide not otherwise produced by a host cell, which is detectable by analysis of the cell or a population of cells, e.g., by the direct fluorometric, radioisotopic, optical or spectrophotometric analysis of the cell or a population of cells and preferably without the need to kill the cells for signal analysis. Preferably, the reporter gene encodes an enzyme that produces a change in at least one fluorescent property of or in the host cell. The at least one fluorescent property is preferably detectable by qualitative, quantitative or semi-quantitative function methods, such as the detection of transcriptional activation. Exemplary enzymes include esterases, phosphatases, proteases (for example, tissue plasminogen activator or urokinase) and other enzymes (such as beta-lactamase or luciferase or sugar hydrolases, such as beta-galactosidase) whose function can be detected by appropriate chromogenic or fluorogenic substrates known to those skilled in the art.

"Plate" refers to a multi-well plate, unless otherwise modified in the context of its usage.

"Sample" refers to any fluid, solid, jelly, emulsion, slurry, or a mixture thereof that contains a membrane compartment. A sample is preferably an aqueous solution that contains a cell, such as a eukaryotic cells, such as a mammalian cell, such as a human cell.

"Signal transduction detection system" refers to a system for detecting signal transduction across a cell membrane, typically a cell plasma membrane. Such systems typically detect at least one activity or physical property directly or indirectly associated with signal transduction. For example, an activity or physical property directly associated with signal transduction is the activity or physical property of either the receptor (e.g., GPCR), or a coupling protein (e.g., a Gα protein). Signal transduction detection systems for monitoring an activity or physical property directly associated with signal transduction, include the detection of GTPase activity and conformational changes of members of the signal transduction system. An activity or physical property indirectly associated with signal transduction is the activity or physical property produced by a molecule other than by either the receptor (e.g., GPCR), or a coupling protein (e.g., a Gα protein) associated with receptor (e.g., GPCR), or a coupling protein (e.g., a Gα protein). Such indirect activities and properties include changes in intracellular levels of molecules (e.g., ions (e.g., $Ca^{++}$, $Na^+$ or $K^+$), second messenger levels (e.g., cAMP, cGMP and inostol phosphate)), kinase activities, transcriptional activity, enzymatic activity, phospholipase activities, ion channel activities and phosphatase activities. Signal transduction detection systems for monitoring an activity or physical property indirectly associated with signal transduction include, for example, transcriptional-based assays, enzymatic assays, intracellular ion assays and second messenger assays.

"Solution fluorescence" refers to fluorescence from a fluorophore in a solution. For instance the fluorophore may be a test chemical (or a component associated with the test compound or a component of the measurement system itself) in an assay buffer. Solution fluorescence is one component of background fluorescence. Background fluorescence may arise from other sources, such as assay vessels (e.g., microtiter plates), optical relay systems and backscatter.

A "target" refers to any biological entity, such as a protein, sugar, carbohydrate, nucleic acid, lipid, a cell or population of cells or an extract thereof, a vesicle, or any combination thereof.

"Transmittance" refers to the fraction of incident light that passes through a medium at a given wavelength. It can also be considered the ratio of radiant power transmitted through a medium to the radiant power incident on the medium at a particular wavelength.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference).

Introduction

The present invention recognizes for the first time that the addition of a photon reducing agent can decrease undesired light emission from a sample. Typically the sample comprises a membrane compartment, using a photon producing agent. The present invention also recognizes for the first time that solution fluorescence in cell-based assays can be reduced by adding a photon reducing agent, such as a dye, to the solution bathing the cells. Aspects of the invention are based, in part, on the counter-intuitive finding that the addition of a chemical having "color" can improve fluorescence assay measurements by reducing solution fluorescence while retaining signal fluorescence from a separate aqueous compartment. The advantages of the present invention include: 1) increasing the signal to noise ratio in assays utilizing membrane compartments, 2) decreasing assay variability, 3) reducing assay time, 4) reducing assay manipulation (especially compared to assays with washing steps), and 5) minimizing solution fluorescence.

As a non-limiting introduction to the breadth of the invention, the invention includes several general and useful aspects, including:

(1) a method for reducing undesirable light emission from a sample (e.g., a biochemical or cellular sample) with at least one photon producing agent by using at least one photon reducing agent (e.g. dye-based photon reducing agents), (2) a method for reducing undesirable light emission from a sample (e.g., a biochemical or cellular sample) with at least one photon producing agent by using at least one collisional quencher, (3) a method for reducing undesirable light emission from a sample (e.g., a biochemical or cellular sample) with at least one photon producing agent by using at least one quencher, such as an electronic quencher, (4) a method of determining bound and free analyte or anti-analyte in a sample using at least one photon reducing agent, (5) a method of screening test chemicals in fluorescent assays using photon reducing agents, (6) compositions, therapeutic compositions and kits for practicing (1), (2), (3), (4), and (5), (7) a system for identifying the compositions of (6), and (8) a method of identifying a chemical with toxicological activity.

These aspects of the invention and others described herein, can be achieved by using the methods and compositions of matter described herein. To gain a full appreciation of the scope of the invention, it will be further recognized that various aspects of the invention can be combined to make desirable embodiments of the invention. For example, the invention includes a method for reducing background fluorescence using dye-based photon reducing agents in assays to identify test chemicals that modulate target proteins. Such combinations result in particularly useful and robust embodiments of the invention.

Methods for Reducing Undesired Light Emission from a Sample Using at Least One Photon Reducing Agent The invention provides for a method of reducing undesirable light emission from a sample. The method can be used with fluorescence assays that are often hampered by solution fluorescence that interferes with detecting a desired signal from the sample. Cell-based assays typically emit solution fluorescence from probes or test chemicals that can obscure desired signal detection. To avoid these problems, the inventors devised a method to reduce undesired light emitted from the sample by adding a photon reducing agent to the sample. As described more fully herein, "photon reducing agent" refers to a molecule that reduces that amount of light from a sample by another molecule.

The method comprises the steps of contacting a sample with at least one photon reducing agent and detecting an optical signal from a photon producing agent. The sample typically comprises a membrane-enclosed compartment in contact with a solid surface that can pass (e.g. transmit) light. The membrane compartment usually includes at least one photon producing agent. As described more fully herein, "photon producing agent" refers to a molecule that emits light. The photon producing agent is typically located either within an aqueous interior of the membrane-enclosed compartment or in association with the membrane or some other component of the membrane compartment (e.g., a cellular organelle). The photon reducing agent is typically located in an aqueous solution that contacts the outer surface of the membrane compartment. The aqueous solution that contacts the outer surface also typically contains the source or sources of light (e.g., photon producing agents) that lead to unwanted light emission from a sample. Photon reducing agents reduce the light emitted from a sample that originates from photon producing agents in the aqueous solution.

Samples in need of a reduction in undesired light emission, as described more fully herein, are typically associated with fluorescent assays and range from chemical or biochemical samples (e.g., vesicles compartmentalizing photon producing agents) to living cell samples (e.g., cell-based assays using reporter genes). Such samples often have solution fluorescence that contributes to increased background fluorescence that can either prevent the measurement of a desired signal or reduce the signal to noise ratio compared to detection of the signal in the presence of a photon reducing agent.

Photon producing agents can be fluorescent protein, such as an Aequorea-related fluorescent protein or a mutant thereof (see, for example, U.S. Pat. No. 5,625,048 to Tsien, issued Apr. 29, 1997; WO 96/23810 to Tsien et al., published Aug. 8, 1996; WO 97/28261 to Tsien et al., published Aug. 7, 1997; PCT/US97/12410 to Tsien et al, filed Jul. 16, 1997; and PCT/US97/14593, filed Aug. 15, 1997), a fluorescent or fluorogenic enzymatic substrate (see, for example, WO 96/30540 to Tsien et al., published Oct. 3, 1996), a member of a FRET pair, or can detect a voltage across a membrane of a cell (see, U.S. Pat. No. 5,661,035 to Tsien et al., issued Aug. 26, 1997), an intracellular ion indicator, such as for calcium ions, such as Fluo3, Fura2, Indo1, or fluorescent labels used in specific binding reactions, such as immunoassays or receptor-ligand assays.

To reduce solution fluorescence, the invention utilizes a photon-reducing agent. Photon reducing agents may be selected to reduce light from another molecule by a mechanism or mechanisms that allow for the reduction of the emission of unwanted light emission from a sample. One class of photon reducing agents may absorb, and therefore reduce, the amount of unwanted light emitted from a sample comprising a photon producing agent.

Desirable photon reducing agents typically have an absorption spectrum that overlaps with the absorption, excitation or emission spectrum (or a combination thereof) of a photon producing agent. Alternatively, another class of photon reducing agents may quench (e.g., by fluorescence resonance energy transfer (FRET)) a photon producing agent. Other quenching mechanisms or agents may be used, including collisional quenchers, electronic quenching, particular quenching, exeplex formation, photo-induced electron transfer, paramagnetic or heavy-atom quenching leading to enhanced intersystem crossing. (see generally, Principles of Fluorescence Spectroscopy by Joseph R. Lakowicz, Plenum Press 1983). Other photon reducing agents are optical interferants that can reduce the amount of light emitted from a photon producing agent by light scatter, refraction or reflectance. For example, particulates reduce light emission from a photon producing agent, in part, by light scattering. It is understood that reduced light emission from a photon producing agent can result from many types of photon reducing agents working with different mechanisms. It is also understood that in certain applications it will be desirable to select photon reducing agents that reduce or decrease undesired light emission from a sample by more than one mechanism. For instance, a photon reducing agent can be selected that reduces solution fluorescence by FRET and has an absorption spectrum that overlaps with the absorption, excitation or emission spectrum of a molecule that produces light. Selection of a photon reducing agent(s) is described more fully herein.

Typically, in a fluorescent assay, at least one photon reducing agent can be selected that has an absorption spectrum that overlaps with the absorption, emission or excitation spectrum of a photon producing agent located outside of a membrane compartment. In some instances the photon producing agent may be located inside and outside the membrane compartment, such as with a membrane permeable sensor that leaks out through the membrane compartment and into the surrounding solution. A photon producing agent can also be free or bound inside a cell, such as a living cell that does not have a cell wall, such as a mammalian cell (such as a human cell. An assay may also include a second photon producing agent in an aqueous solution surrounding the membrane compartment or at a site other than the site of desirable signal emission. The number of photon reducing agents in an assay typically ranges from between 1 and 5, between 1 and 4, between 1 and 3, between 1 and 2, and may include at least two or more or at least three or more. For example, the first photon producing agent may be a reporter gene substrate or product located inside of a cell, and the second photon producing agent may be a test chemical in the bathing solution.

Photon reducing agents can be readily selected for an absorption spectrum that overlaps with the absorption, emission or excitation spectrum of a photon producing agent. As described herein, the absorption spectra of a photon reducing agent can be readily measured and compared to measured absorption, emission or excitation spectrum of a known or expected photon producing agent. Such known or expected photon producing agents include, fluorescent reporter substrates, fluorescent labels, fluorescent membrane sensors, fluorescent proteins, test chemicals and intracellular analyte indictors (e.g., ion chelators). Methods known or developed in the art for measuring and comparing absorption spectra can also be used to identify photon reducing agents. Light reducing dyes refer to photon reducing agents that have an absorption spectrum that overlaps with the absorption, emission or excitation spectrum of a photon producing agent.

When selecting a photon reducing agent, such as a light reducing dye, it is advantageous to compare the extent of its absorption spectrum overlap with 1) the absorption, emission or excitation spectrum of a photon producing agent in aqueous solution and 2) the absorption, emission or excitation spectrum of the expected signal molecule in an assay sample. This comparison can aid in the selection of a photon reducing agent, such as a light reducing dye, by optimizing the spectral overlaps. In addition, it is desirable to select photon reducing agents with high extinction coefficients in order to reduce the amount of photon reducing agent needed for the desired effect.

Preferable photon reducing agents typically at least partially block either or both of the excitation or emission wavelengths of photon producing agents. In doing so, preferable photon reducing agents reduce undesired light emission from a sample. Such preferable photon reducing agents can be determined by comparing the extinction coefficients of candidate photon reducing agents with the expected photon producing agents at the desired wavelength or range of wavelengths, by empirical observations, or by routine experimentation to select such desired photon producing agents using the methods of the present invention. Photon reducing agents can reduce the emission of undesired light from a sample by at least about 10 percent, preferably at least about 30 percent, more preferably at least about 50, and most preferably between about 70 and 99 percent as compared to light emission from a sample or a particular photon producing agent in the absence of a photon reducing agent.

Such photon producing agents and photon reducing agents can be determined, for example, by exciting a sample comprising a photon producing agent and a photon reducing agent with light of a first wavelength bandwidth and collecting the emission from the sample at a second wavelength bandwidth. Preferably, the first wavelength bandwidth and the second wavelength bandwidth do not overlap, but they may. Preferable first wavelength bandwidths and preferable second wavelength bandwidths can be determined by routine experimentation using methods of the present invention to determine such wavelength bandwidth ranges and overlaps. Such bandwidths preferably include the appropriate excitation or emission peaks of at least one of the photon producing agent or photon reducing agent, but that need not be the case because significant excitation or emission can be obtained over a large portion of the appropriate excitation spectra or emission spectra.

Photon reducing agents are preferably provided at a working concentration in a sample between about 0.1 mM and about 10 mM and more preferably between about 0.5 mM and 5 mM. When two or more photon reducing agents are present in a sample, the combined concentration of the photon reducing agents is preferably between about 0.1 mM and 10 mM and more preferably between about 0.5 mM and 5 mM. Photon reducing agents can increase the signal-to-noise ration of an assay by between about 50% to about 100,000% or greater, and preferably between about 500% and about 3,000%. The percent increase in signal-to-noise ratio (S/N) in the presence of a photon reducing agent (PRA) can be calculated by the formula ((S/N in the presence of a PRA)/(S/N in the absence of a PRA))×100=percent increase in S/N.

Photon reducing agents also can be substantially impermeant to the membrane of a membrane compartment. Substantially impermeant, in this instance, means that under assay conditions, the concentration of the photon reducing agent within the membrane compartment is less than 50%, preferably less than 30%, and most preferably less than 10% of the concentration outside the membrane compartment.

Preferable photon reducing agents have a partition coefficient (octanol/water) equal to or less than CCF2/AM, at a pH between about 6 and 8, preferably about pH 7, so that the photon reducing agent preferably partitions in an aqueous solution rather than in a hydrophobic phase, such as a membrane (for CCF2/AM, see U.S. Pat. No. 5,741,657 to Tsien et al., issued Apr. 21, 1998). Also, preferable photon reducing agents have solubility in water of at least about 1 mM and preferably at least about 10 mM under assay conditions, such as between about 4° C. and 42° C., preferably between about 24° C. and 37° C. In addition, photon reducing agents are preferably should be more impermeant across a membrane compartment, such as a mammalian cell, than a photon producing agent used in an assay. Photon reducing agents can be a pH indicator dye and be dyes, such as azo dyes.

Preferable photon reducing agents also have an extinction coefficient of between about 2,000 $M^{-1}$ $cm^{-1}$ to about 500,000 $M^{-1}$ $cm^{-1}$, preferably between about 10,000 $M^{-1}$ $cm^{-1}$ and 200,000 $M^{-1}$ $cm^{-1}$, and more preferably greater than 10,000 $M^{-1}$ $cm^{-1}$ at a wavelength range of wavelengths used in an assay.

In many instances the photon producing agent that leads to unwanted light emitted from the sample will be the signal molecule in a non-desired location or compartment. Such instances typically occur when the signal molecule is present in the surrounding solution and reducing solution fluorescence becomes desirable. For example, a fluorescent reporter that leaks out of a membrane compartment, such as a cell, will often decrease the signal to noise ratio of the assay. When the photon producing agent is the signal molecule, it is desirable to select a light reducing dye having an absorption spectrum that significantly overlaps with the absorption, emission or excitation spectrum of the expected signal molecule. Preferably, such photon reducing agents can be identified by determining the percentage overlap of spectrum as determined from the concentration and extinction coefficient of a photon producing agent and a photon reducing agent at a desired wavelength or range of wavelengths (see, Lakowicz, J. R. Principles of Fluorescence Spectroscopy, New York: Plenum Press (1983)). Generally, the wavelength range for such spectra is about 260 nm to about 900 nm, although narrow ranges can be used, such as about 290 to 800 nm, and about 300 to 700 nm. In addition it is advantageous to select a photon reducing agent with an optical density or extinction coefficient sufficiently high to be effective in reducing solution fluorescence.

In one embodiment of the invention, a photon producing agent is excited with light of a narrow wavelength bandwidth, such as light filtered through a band pass excitation filter or by excitation with a narrow wavelength band or single wavelength of laser light as is known in the art. The emission from the sample is detected using a selected bandwidth of light emitted from the photon producing agent using, for example, an emission band pass filter. Preferably, the photon reducing agent has a high extinction coefficient at the excitation and emission wavelengths.

Depending on the sensitivity or reactivity of the reagents used in the assay, such as membrane compartments (such as cells) or targets, it will be desirable to select photon reducing agents with little or no relevant biological activity so that the photon reducing agent does not interfere with an assay. Often it will be valuable to test the toxicity and non-specific binding of the photon reducing agents in the assay to insure their compatibility with assay components. Preferably, photon reducing agents are not toxic to cells used in a cell based assay within the time frame of the assay. Preferably, photon reducing agents do not react with, or bind to, the targets or other biomolecules in the assay to undesirably alter the biological activity or property being measured. Preferably, photon reducing agents should not cross the (cell) membrane.

Samples can comprise one or more or two or more photon producing agents and one or more or two or more photon reducing agents. In the case of multiple photon producing agents or photon reducing agents, the characteristics of the photon producing agents or photon reducing agents can be selected to have desired characteristics. For example, photon reducing agents can be selected to form combinations that have absorption spectra that are broader than the absorption spectra of the individual photon reducing agents. These combinations of photon reducing agents can be used to reduce the emission of undesired light from one or more photon producing agents in a sample. Such reduced emission of undesired light from the sample can be accomplished during the excitation of and emission from the photon producing agent.

Light emitted from a sample can be detected by any appropriate means for a particular assay format. For example, fluorescence can be detected using a fluorometer, which can detect epifluorescence. Samples can be provided in any appropriate container from which a signal can be detected, such as vials or wells of a microtiter plate. For microtiter plates, the number of wells in a standard 96-well format footprint can be between about 6 and about 3,456 wells, preferably between about 96 wells and 864 wells, and more preferably between about 288 and about 384 wells, more preferably greater than about 384 wells (see, U.S. patent application Ser. No. 08/868,018 to Coassin et al., filed Jun. 3, 1997). Preferably, the microtiter plate has wells that have a bottom that has at least a portion that can pass light of a wavelength used in an assay. Membrane compartments in the sample preferably are in contact (physical contact or optical contact) with the bottom of such wells. In this instance, optical contact means that the presence of a photon reducing agent, at least a portion of the light emitted from said membrane compartment can pass through the bottom of said well. The solution volume containing the sample used is dependent upon the volume capacity of the container used in an assay. Preferably, the sample volume is between about 100 nanoliters and about 1 milliliter, preferably between about 0.5 microliters and about 0.5 milliliter, and most preferably between about 1 microliters and about 250 microliters or between about 3 microliters and about 100 microliters.

The number of membrane compartments, such as cells, in a sample is preferably between about 10 and about 1,000,000,000 membrane compartments and more preferably between about 100 and about 200,000 membrane compartments. When the membrane compartments are cells, the cells are preferably living, and are preferably mammalian cells. Samples can contain a predetermined number of cells or an unknown number of cells. Samples can contain cells that are members of a clonal population or a heterogeneous population. Preferably, the membrane compartments form a single layer of membrane compartments in optical contact with an appropriate solid surface such that the emission from a photon producing agent can pass through the appropriate solid surface. However, the membrane compartments may form a plurality of such layers. Membrane compartments in optical contact with a solid surface can be in direct contact with the solid surface, preferably between about 5 Å to about the thickness of a eukaryotic cell in culture, more preferably between about 5 Å to about one-half the thickness of a eukaryotic cell in culture, more preferably between about 10 Å to about the thickness of two IgG antibodies placed Fab region to Fab region, more preferably between about 15 Å and about the thickness of a lipid bilayer or about the thickness of a cytoplasmic membrane of a eurkaryotic cell in culture.

Cells

Many cells can be used in the invention for cell based assays. Such cells include, but are not limited to; baby hamster kidney (BHK) cells (ATCC No. CCL10), mouse L cells (ATCC No. CCLI.3), Jurkats (ATCC No. TIB 152) and 153 DG44 cells (see, Chasin (1986) Cell. Molec. Genet. 12: 555) human embryonic kidney (HEK) cells (ATCC No. CRL1573), Chinese hamster ovary (CHO) cells (ATCC Nos. CRL9618, CCL61, CRL9096), PC12 cells (ATCC No. CRL17.21), COS-7 cells (ATCC No. CRL1651) and yeast. Preferred cells for heterologous cell surface protein expression are those that can be readily and efficiently transfected. Preferred cells include Jurkat cells, CHO cells, and HEK 293 cells, such as those described in U.S. Pat. No. 5,024,939 and by Stillman et al. (1985) Mol. Cell. Biol. 5: 2051–2060, each of which are incorporated herein by reference.

Targets

One method of the present invention uses targets for identifying chemicals that are useful for modulating the activity of the target or a target having similar structural or functional characteristics. The target can be any biological entity, such as a protein, sugar, nucleic acid or lipid. Typically, targets will be proteins such as enzymes or cell surface proteins. Targets can be assayed in either biochemical assays (targets free of cells) or cell based assays (targets associated with a cell).

For example, cells may be loaded with ion or voltage sensitive dyes to report receptor or ion channel activity, such as calcium channels, or N-methyl-D-aspartate (NMDA) receptors, GABA receptors, kainate/AMPA receptors, nicotinic acetylcholine receptors, sodium channels, calcium channels, potassium channels, excitatory amino acid (EAA) receptors, and nicotinic acetylcholine receptors. Assays for determining activity of such receptors can also use agonists and antagonists to use as negative or positive controls to assess the activity of tested chemicals. In preferred embodiments of automated assays for identifying chemicals that have the capacity to modulate the function of receptors or ion channels (e.g., agonists, antagonists), changes in the level of ions in the cytoplasm or membrane voltage will be monitored using an ion-sensitive or membrane voltage fluorescent indicator, respectively. Among the ion-sensitive indicators and voltage probes that may be employed are those disclosed in the Molecular Probes 1997 Catalog, herein incorporated by reference.

Other methods of the present invention concern determining the activity of receptors. Receptor activation can sometimes initiate subsequent intracellular events that release intracellular stores of calcium ions for use as a second messenger or the influx of calcium ions into a cell. Activation of some G-protein-coupled receptors stimulates the formation of inositol triphosphate (IP3 a G-protein coupled receptor or tyro sine kinase second messenger) through phospholipase C-mediated hydrolysis of phosphatidylinositol, Berridge and Irvine (1984), Nature 312: 315–21. IP3 in turn stimulates the release of intracellular calcium ion stores. Thus, a change in cytoplasmic calcium ion levels caused by the release of calcium ions from intracellular stores can be used to reliably determine G-protein-coupled receptor function. Among G-protein-coupled receptors are muscarinic acetylcholine receptors (mAChR), adrenergic receptors, serotonin receptors, dopamine receptors, angiotensin receptors, adenosine receptors, bradykinin receptors, metabotropic excitatory amino acid receptors, and the like. Cells expressing such G-protein-coupled receptors may exhibit increased cytoplasmic calcium levels as a result of contribution from both intracellular stores and via activation of ion channels. In such instances, it may be desirable, although not necessary, to conduct such assays in calcium-free buffer, optionally supplemented with a chelating agent such as EGTA, to distinguish fluorescence response resulting from calcium release from internal stores.

Exemplary membrane proteins that may be targets include, but are not limited to, surface receptors and ion channels. Surface receptors include, but are not limited to, muscarinic receptors, e.g., human M2 (GenBank accession #M16404); rat M3 (GenBank accession #M16407), human M4 (GenBank accession #M16405), human M5 (Bonner, et al., (1988) Neuron 1, pp. 403–410); and the like. Neuronal nicotinic acetylcholine receptors include, e.g., the human $\alpha 2$, $\alpha 3$, and $\beta 2$, subtypes, the human $\alpha 5$ subtype (Chini, et al. (1992) Proc. Natl. Acad. Sci. U.S.A. 89: 1572–1576), the rat $\alpha 2$ subunit (Wada, et al. (1988) Science 240, pp. 330–334), the rat $\alpha 3$ subunit (Boulter, et al. (1986) Nature 319, pp. 368–374), the rat $\alpha 4$ subunit (Goldman, et al. (1987) Cell 48, pp. 965–973), the rat $\alpha 5$ subunit (Boulter, et al. (1990) I. Biol. Chem. 265, pp. 4472–4482), the chicken $\alpha 7$ subunit (Couturier et al. (1990) Neuron 5: 847–856), the rat $\beta 2$ subunit (Deneris, et al. (1988) Neuron 1, pp. 45–54), the rat $\beta 3$ subunit (Deneris, et al. (1989) J. Biol. Chem. 264, pp. 6268–6272), the rat $\beta 4$ subunit (Duvoisin, et al. (1989) Neuron 3, pp. 487–496), combinations of the rat $\alpha$ subunits, $\beta$ subunits and a and p subunits. GABA receptors include, e.g., the bovine n, and p, subunits (Schofield, et al. (1987) Nature 328, pp. 221–227), the bovine n, and a, subunits (Levitan, et al. (1988) Nature 335, pp. 76–79), the $\gamma$-subunit (Pritchett, et al. (1989) Nature 338, pp. 582–585), the p, and p, subunits (Ymer, et al. (1989) EMBO J. 8, pp. 1665–1670), the 6 subunit (Shivers, B. D. (1989) Neuron 3, pp. 327–337), and the like. Glutamate receptors include, e.g., rat GluR1 receptor (Hollman, et al. (1989) Nature 342, pp. 643–648), rat GluR2 and GluR3 receptors (Boulter et al. (1990) Science 249:1033–1037, rat GluR4 receptor (Keinanen et al. (1990) Science 249: 556–560), rat GluR5 receptor (Bettler et al. (1990) Neuron 5: 583–595), rat GluR6 receptor (Egebjerg et al. (1991) Nature 351: 745–748), rat GluR7 receptor (Bettler et al. (1992) neuron 8:257–265), rat NMDAR1 receptor (Moriyoshi et al. (1991) Nature 354:31–37 and Sugihara et al. (1992) Biochem. Biophys. Res. Comm. 185:826–832), mouse NMDA el receptor (Meguro et al. (1992) Nature 357: 70–74), rat NMDAR2A, NMDAR2B and NMDAR2C receptors (Monyer et al. (1992) Science 256: 1217–1221), rat metabotropic mGluR1 receptor (Houamed et al. (1991) Science 252: 1318–1321), rat metabotropic mGluR2, mGluR3 and mGluR4 receptors (Tanabe et al. (1992) Neuron 8:169–179), rat metabotropic mGluR5 receptor (Abe et al. (1992) I. Biol. Chem. 267: 13361–13368), and the like. Adrenergic receptors include, e.g., human pl (Frielle, et al. (1987) Proc. Natl. Acad. Sci. 84, pp. 7920–7924), human $\alpha 2$ (Kobilka, et al. (1987) Science 238, pp. 650–656), hamster $\beta 2$ (Dixon, et al. (1986) Nature 321, pp. 75–79), and the like. Dopamine receptors include, e.g., human D2 (Stormann, et al. (1990) Molec. Pharm. 37, pp. 1–6), mammalian dopamine D2 receptor (U.S. Pat. No. 5,128,254), rat (Bunzow, et al. (1988) Nature 336, pp. 783–787), and the like. NGF receptors include, e.g., human NGF receptors ( Johnson, et al. (1986) Cell 47, pp. 545–554), and. the like. Serotonin receptors include, e.g., human 5HT1a (Kobilka, et al. (1987) Nature 329, pp. 75–79), serotonin 5HT1C receptor (U.S. Pat. No. 4,985,352), human 5HT1D (U.S. Pat. No. 5,155,218), rat 5HT2 (Julius, et al. (1990) PNAS 87, pp.928–932), rat 5HT1c (Julius, et al. (1988) Science 241, pp. 558–564), and the like.

Ion channels include, but are not limited to, calcium channels comprised of the human calcium channel $\alpha 2$ $\beta$ and/or $\gamma$-subunits (see WO89/09834; human neuronal $\alpha 2$ subunit), rabbit skeletal muscle al subunit (Tanabe, et al. (1987) Nature 328, pp. 313-E318), rabbit skeletal muscle $\alpha 2$ subunit (Ellis, et al. (1988) Science 241, pp. 1661–1664), rabbit skeletal muscle p subunit (Ruth, et al. (1989) Science 245, pp. 1115–1118), rabbit skeletal muscle $\gamma$ subunit (Jay, et al. (1990) Science 248, pp. 490–492), and the like. Potassium ion channels include, e.g., rat brain (BK2) (McKinnon, D. (1989) J. Biol Chem. 264, pp. 9230–8236), mouse brain (BK1) (Tempel, et al. (1988) Nature 332, pp. 837–839), and the like. Sodium ion channels include, e.g., rat brain I and II (Noda, et al. (1986) Nature 320, pp. 188–192), rat brain III (Kayano, et al. (1988) FEBS Lett. 228, pp. 187–1.94), human II (ATCC No. 59742, 59743 and Genomics 5: 204–208 (1989), chloride ion channels (Thiemann, et al. (1992), Nature 356, pp. 57–60 and Paulmichl, et al. (1992) Nature 356, pp. 238–241), and others known or developed in the art.

Intracellular receptors may also be used as targets, such as estrogen receptors, glucocorticoid receptors, androgen receptors, progesterone receptors, and mineralocorticoid receptors, in the invention. Transcription factors and kinases can also be used as targets, as well as plant targets.

Various methods of identifying activity of a chemical with respect to a target can be applied, including: ion channels (PCT publication WO 93/13423), intracellular receptors (PCT publication WO 96/41013), U.S. Pat. Nos. 5,548,063, 5,171,671, 5,274,077, 4,981,784, EP 0 540 065 A1, U.S. Pat. Nos. 5,071,773, and 5,298,429. Fluorescent assays that can be used with the invention include those described in PCT WO 96/3540 (Tsien), PCT WO 96/41166 (Tsien) and PCT WO 96/23810 (Tsien). The methods set forth in PCT WO 96/3540 (Tsien) and PCT WO 96/23810 (Tsien) can also be combined with methods described in U.S. Pat. Nos. 5,401, 629 and 5,436,128 by Harpold et al. for assays of cell surface receptors and the cell based intracellular receptor assays referenced herein. All of the foregoing references are herein incorporated by reference in their entirety.

Fluorescence Measurements

When using fluorescent sensors, indicators or probes such as photon producing agents, it will be recognized that different types of fluorescent monitoring systems can be used to practice the invention. Preferably, FACS systems or systems dedicated to high throughput screening, e.g 96 well or greater microtiter plates or multi-well platforms are used to identify compounds such as therapeutic compounds and to assess the toxicology of such compounds (see U.S. application Ser. No. 08/858,016 to Stylli et al, filed May 16, 1997). Such high throughput screening systems can comprise, for example:

a) a storage and retrieval module for storing a plurality of chemicals in solution in addressable chemical wells, a chemical well retriever, and having programmable selection and retrieval of said addressable chemical wells, and having a storage capacity for at least 100,000 said addressable wells, wherein at least one of said addressable wells comprises a photon reducing agent, b) a sample distribution module comprising a liquid handler to aspirate or dispense solutions from selected said addressable chemical wells, said chemical distribution module having programmable selection of, and aspiration from, said selected addressable chemical wells and programmable dispensation into selected addressable sample wells, and said liquid handler can dispense into arrays of addressable wells with different densities of addressable wells per centimeter squared, c) a sample transporter to transport said selected addressable chemical wells to said sample distribution module and optionally having programmable control of transport of said selected addressable chemical wells, d) a reaction module comprising either a reagent dispenser to dispense reagents into said selected addressable sample wells or a fluorescent detector to detect chemical reactions ins said selected addressable sample wells, and e) a data processing and integration module, wherein said storage and retrieval module, said sample distribution module, and said reaction module are integrated and programmably controlled by said data processing and integration module; and said storage and retrieval module, said sample distribution module, said sample transporter, said reaction module and said data processing and integration module are operably linked to facilitate rapid processing of said addressable sample wells.

Multi-well platforms useful in the present invention can have between about 6 and about 5,000 wells, preferably between about 96 and about 4,000 wells, most preferably in multiples of 96 (see U.S. patent application Ser. No. 08/867,567, filed Jun. 2, 1997; U.S. patent application Ser. No. 08/868,018, filed Jun. 3, 1997; U.S. patent application Ser. No. 08/867,584, filed Jun. 2, 1997; U.S. patent application Ser. No. 08/868,049, filed Jun. 3, 1997; U.S. patent application Ser. No. 09/030,578, filed Feb. 24, 1998; and U.S. patent application Ser. No. 09/028,283, filed Feb. 24, 1998). Methods of performing assays on fluorescent materials are well known in the art and are described in, e.g., Lakowicz, J. R., Principles of Fluorescence Spectroscopy, New York:Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219–243; Turro, N.J., Modem Molecular Photochemistry, Menlo Park: Benjamin/Cummings Publishing Col, Inc. (1978), pp. 296–361.

The present invention can be used to increase the signal-to-noise ratio in fluorescence activated cell sorting (FACS). In this aspect of the invention, the membrane compartment comprises at least one photon producing agent and the surrounding solution exhibits unwanted optical background (such as fluorescence) from, for example, at least one photon producing agent. In this embodiment of the invention, the sample volume is preferably a small droplet comprising the membrane compartment, such as are useful in FACS analysis. The optical path length through the droplet is preferably only a few micrometers, so that the reduction of the excitation light or absorption of the emitted fluorescence by absorptive filtering in the droplet is small. Significant reduction of unwanted solution fluorescence from the droplet can be achieved under such conditions when the photon reducing agent in the droplet can interact with the excited state of the molecule which is the source of the unwanted solution fluorescence. Interactions that give rise to such beneficial reduction in unwanted solution fluorescence include, but are not limited to, fluorescence resonance energy transfer, collision quenching, ground state dark complex formation, paramagnetic enhancement of intersystem crossing, Dexter exchange coupling, photo-induced electron transfer. The common property of these interactions is that they occur over molecular distances of less than about 20 nm, and comprise a form of energy transfer other than simple absorption due to inner filtering. The particular conditions for this aspect of the invention can be determined using routine experimentation using the methods of the present invention.

Fluorescence in a sample can be measured using a fluorimeter. In general, excitation radiation from an excitation source having a first wavelength passes through excitation optics. The excitation optics allow the excitation radiation to excite the sample. In response, fluorescent probes in the sample emit radiation that has a wavelength that is different from the excitation wavelength. Collection optics then collect the emission from the sample. The device can include a temperature controller to maintain the sample at a specific temperature while it is being measured. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Preferably, fluorescence resonance energy transfer (FRET), can be used as a way of monitoring activity inside a cell, such as with the reporter gene system described in Tsien et al (PCT WO96/30540). The degree of FRET can be determined by any appropriate spectral or fluorescence lifetime characteristic of the excited construct. For example, the degree of FRET can be measured by determining the intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor. For example, cleavage of the linker increases the intensity of fluorescence from the donor, decreases the intensity of fluorescence from the acceptor, increases the ratio of fluorescence amplitudes from the donor to that from the acceptor, and increases the excited state lifetime of the donor.

As would be readily appreciated by those skilled in the art, the efficiency of fluorescence resonance energy transfer depends on the fluorescence quantum yield of the donor fluorophore, the orientation of the fluorophore, the donor-acceptor distance, and the overlap integral of donor fluorescence emission and acceptor absorption. The energy transfer is most efficient when a donor fluorophore with high fluorescence quantum yield (preferably, one approaching 100%) is paired with an acceptor with a large extinction coefficient at wavelengths coinciding with the emission of the donor. The dependence of fluorescence energy transfer on the above parameters has been reported (Forster, T. (1948) Ann.Physik 2: 55–75; Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, Vol 30, ed. Taylor, D. L. & Wang, Y.-L., San Diego: Academic Press (1989), pp. 219–243; Turro, N. J., Modern Molecular Photochemistry, Menlo Part: Benjamin/Cummings Publishing Co., Inc. (1978), pp. 296–361). Also, tables of spectral overlap integrals are readily available to those working in the field (for example, Berlman, I. B. Energy transfer parameters of aromatic compounds, Academic Press, New York and London (1973)). The distance between the donor and acceptor at which FRET occurs with 50% efficiency is termed $R_0$ and can be calculated from the spectral overlap integrals. For the donor-acceptor pair fluorescein-tetramethyl rhodamine, which is frequently used for distance measurement in proteins, this distance $R_0$ is around 50–70 Å (dos Remedios, C. G. et al. (1987) J. Muscle Research and Cell Motility 8:97–117). The distance at which the energy transfer in this pair exceeds 90% is about 45 Å.

Preferably, changes in the degree of FRET are determined as a function of the change in the ratio of the amount of fluorescence from the donor and acceptor, an analysis process referred to as "ratioing." Changes in the absolute amount of substrate, excitation intensity, and turbidity or other background absorbances in the sample at the excitation wavelength affect the intensities of fluorescence from both the donor and acceptor approximately in parallel. Therefore, the ratio of the two emission intensities is a preferred and more robust measure of cleavage than either intensity alone.

The excitation state lifetime of the donor moiety is, likewise, independent of the absolute amount of substrate, excitation intensity, or turbidity or other background absorbances. Its measurement requires equipment with nanosecond time resolution, except in the special case of transition metal complexes, such as lanthanide complexes, in which case microsecond to millisecond resolution is sufficient.

The ratiometric fluorescent reporter system described herein has significant advantages over existing reporters for gene integration analysis, as it allows sensitive detection and isolation of both expressing and non-expressing single living cells. This assay system uses a non-toxic, non-polar fluorescent substrate that is easily loaded and then trapped intracellularly. Cleavage of the fluorescent substrate by beta-lactamase yields a fluorescent emission shift as substrate is converted to product. Because the beta-lactamase reporter readout is ratiometric, it is unique among reporter gene assays because it controls for variables such as the amount of substrate loaded into individual cells. The stable, easily detected, intracellular readout eliminates the need for establishing clonal cell lines prior to expression analysis.

Method of Reducing Undesired Light Emission from a Sample that Includes an Anti-Analyte or Analyte Using at Least One Photon Reducing Agent The present invention also includes a method of reducing undesired light emission from a sample that includes an anti-analyte (or an analyte). The anti-analyte (or analyte) can be part of a membrane compartment, for example, on the surface of such membrane compartment. This method includes contacting a sample in need of reduction of undesired light reduction with at least one photon reducing agent. The sample includes an anti-analyte (or an analyte) in contact with a solid surface that can pass light and said anti-analyte (analyte) optionally has a bound analyte (anti-analyte), said analyte (anti-analyte) includes at least one first photon producing agent that is in an aqueous solution that contacts said anti-analyte (analyte). An optical signal from said first photon producing agent is detected. The photon reducing agent can be any photon reducing agent, but is preferably is a collisional quencher or electronic quencher that is selected to quench fluorescence from a first photon producing agent and/or from a second photon producing agent in a sample.

The present invention also includes a method of determining bound and free analyte (or anti-analyte) in a sample by detecting fluorescence from a sample that contains an anti-analyte (or analyte) in contact with a solid surface that can transmit light and an analyte (or anti-analyte) that includes at least one photon producing agent. The amount of fluorescence from the photon producing agent is detected. The sample is then contacted with at least one photon reducing agent, and the fluorescence from the photon producing agent is detected. The apparent amount of analyte (or anti-analyte) bound to the anti-analyte (or analyte) is then determined as the difference in fluorescence between the amount of fluorescence in an appropriate control sample. Preferably, the photon reducing agent has an absorption spectra that overlaps with the absorption, emission or excitation spectrum of said first photon producing agent. Also, the first photon producing agent of said analyte can transfer fluorescence resonance energy to the photon reducing agent when the analyte is free in said aqueous solution.

In these methods, an anti-analyte or an analyte can be any anti-analyte-analyte pair, as this term is understood in the art, including a binding pair. Anti-analyte-analyte pairs include for example, receptor-ligand pairs, antibody-antigen pairs, nucleic acid hybridization pairs, nucleic acid-protein pairs, or combinations thereof as are known in the art. Anti-analytes and analytes include, for example, receptors, ligands, immunogloblins of any class or subclass, an active fragment of any of the above, chemicals, drugs, toxins, biological material such as proteins, polypeptides, peptides, carbohydrates, lipids, nucleic acids such as DNA or RNA, or combinations thereof. An anti-analyte or analyte can be associated with a membrane compartment, such as being on the surface of a membrane compartment, such as the external surface of the membrane compartment.

In these methods, the anti-analyte or analyte can be in contact with a solid surface. The solid surface can be a container used in an assay, such as a vial or a well of a microtiter plate. Preferably, the solid surface is the bottom of a well of a microtiter plate, wherein the bottom has at least a portion that can transmit light of a wavelength used in an assay. Analytes or anti-analytes can be bound to sold surfaces by a variety of means, such as through gluteraldehyde cross-linking, electrostatic absorption, passive absorption, or covalent linkage (see, for example, Harlow, Antibodies, Cold Spring Harbor Press, Cold Spring Harbor, 1988; and Sambrook et al., Molecular Cloning: A Laboratory Manual, Cold Spring Harbor Press, Cold Spring Harbor, 1989)). Furthermore, anti-analytes or analytes can be labeled with a photon producing agent, such as a fluorescent moiety, using methods known in the art (see, Harlow, supra, 1988; and Sambrook et al., supra, 1989).

The methods of the present invention can be used in any anti-analyte-analyte detection assay that uses a label. For use in the present invention, the label need only be replaced with a photon producing agent. Such known assays are direct non-competitive assays (U.S. Pat. Nos. 4,187,075 and 4,497,900), competitive binding (U.S. Pat. Nos. 4,134,792; 3,654,090; 4,478,946; 4,092,408; 4,478,946; 4,371,140; 4,228,237; 4,490,473; 4,243,749; 4,298,685; 3,839,153; 4,048,298; and 4,271,140), sequential saturation (U.S. Pat. Nos. 4,134,792; 4,271,140; and 4,048,298), displacement or release assay (U.S. Pat. Nos. 4,120,945; 4,256,725; and 4,388,295), homogeneous assays (U.S. Pat. No. 4,680,275), one-site immunometric (U.S. Pat. Nos. 4,134,792; 3,654,090; 4,134,792; 3,850,752; 4,670,383; 4,332,495; 4,034,074; 4,434,236; EP No. 177,191; and GB 2,084,317), and sandwich assays (U.S. Pat. Nos. 4,134,792; 4,376,110; 4,478,946; 4,271,140; 4,034,074; 4,474,892; 4,230, 683; 4,228,683; 4,228,237; 4,098,876; 4,376,110; 4,486,530; 4,376,110; 4,486,530; 4,271,140; and 4,343,896), or any other such method known in the art or later developed.

A generic example of a method of the present invention is as follows. An anti-influenzavirus antibody is immobilized upon the clear bottom of a well of a microtiter plate using known methods. This structure is contacted with a sample that contains influenzavirus labeled with a photon producing agent, unlabeled influenzavirus, and at least one photon reducing agent. These mixtures are allowed to incubate under appropriate conditions, after which the fluorescence of the sample is determined by exciting the bottom of the microtiter well with light of an appropriate wavelength and measuring the emission of a wavelength appropriate for the photon producing agent from the bottom of the microtiter well. The amount of emission is compared to appropriate controls, such as positive and negative controls determined at the same time or at a separate time. The relative amount of emission is correlated to the presence of concentration of the unlabeled influenzavirus in the sample. In the alternative, the photon reducing agent can be added to the sample at any time during the course of the assay. The photon reducing agent serves to reduce the amount of undesired light emission from the sample (for example, from the unbound influenza virus and other components of the sample), which can increase the signal-to-noise ratio of the assay and thus increase the sensitivity and precision of the assay.

This method can also be used to determine the relative amount of free and bound influenza virus using methods of the present invention. For example, influenzavirus labeled with a fluorescent label can be present in the sample and anti-influenzavirus antibody can be immobilized on the bottom of the microtiter well. The fluorescence from the sample from the bottom of the microtiter well is then measured (first fluorescence) to determine total fluorescence. Then an photon reducing agent is added to the sample and fluorescence from the sample is measured again from the bottom of the microtiter well (second fluorescence). The difference between the second fluorescence to the first fluorescence is a measure of the amount of bound influenzavirus and free influenzavirus in the sample.

Method of Screening Test Chemicals in Fluorescent Assays Using at Least One Photon Reducing Agent The present invention also includes a method of identifying a chemical with a biological activity (including toxicological activities). The method is performed by contacting a sample with a test chemical, wherein the sample comprises a target and a photon producing agent. The sample is also contacted with at least one photon reducing agent and the optical signal from the photon producing agent is detected. The photon reducing agent may be added before or after the test chemical, as appropriate. The sample can include a membrane compartment in contact with a solid surface that can pass light. The membrane compartment includes at least one photon producing agent that directly or indirectly monitors the activity of the target. The photon reducing agent is in an aqueous solution that contacts the outer surface of said membrane compartment. Preferably, the photon reducing agent has an absorption spectra that overlaps with the absorption, emission or excitation spectrum of the photon producing agent or of a second photon producing agent in said aqueous solution. Also, the first photon producing agent can, in some instances, transfer fluorescence resonance energy to the photon reducing agent. Alternatively, the second photon producing agent in an aqueous solution can transfer fluorescence resonance energy to the photon reducing agent. The present invention also includes a therapeutic compound or composition identified by this method.

A test chemical with a biological activity, such as a therapeutic, can be identified by contacting a test chemical suspected of having a biological activity with a sample comprising a membrane compartment comprising a target, such as a mammalian cell comprising a receptor. In some assays, the binding of a test chemical with a target can result in the expression of a reporter gene in the membrane compartment. The reporter gene can encode a photon producing agent or precursor photon producing agent, or encode an enzyme that can produce a photon producing agent from an appropriate substrate. If the sample contains a test chemical with a biological activity reported by the reporter gene, then the amount of a fluorescent reporter product in the sample, such as inside or outside of the cell, will either increase or decrease relative to background or control levels. The amount of the fluorescent reporter product is measured by exciting the fluorescent reporter product with an appropriate radiation of a first wavelength and measuring the emission of radiation of a second wavelength emitted from said sample. The amount of emission is compared to background or control levels of emission. If the sample having the test chemical exhibits increased or decreased emission relative to that of the control or background levels, then a candidate modulator has been identified. The amount of emission is related to the amount or potency of the therapeutic in the sample. Such methods are described in, for example, Tsien (PCT/US90/04059). Such methods identify candidate modulators of biological processes. The candidate modulator can be further characterized and monitored for structure, potency, toxicology, and pharmacology using well known methods or those described herein.

The signal-to-noise ratio of such assays can be increased by the addition of at least one photon reducing agent during the course of such assays. The addition of at least one photon reducing agent can also increase the sensitivity and precision of such assays.

The structure of a candidate modulator identified by the invention can be determined or confirmed by methods known in the art, such as mass spectroscopy and nuclear magnetic resonance (NMR). For putative chemicals with a biological activity stored for extended periods of time, the structure, activity, and potency of candidate modulators can be confirmed.

Depending on the system used to identify candidate modulators, a candidate modulator can have putative pharmacological activity. For example, if the candidate modulator is found to inhibit T-cell proliferation (activation) in vitro, then the candidate modulator would have presumptive pharmacological properties as an immunosuppressant or anti-inflammatory (see, Suthanthiran et al., *Am. J. Kidney Disease,* 28:159–172 (1996)). Such nexuses are known in the art for several disease states, and more are expected to be discovered over time. Based on such nexuses, appropriate confirmatory in vitro and in vivo models of pharmacological activity, as well as toxicology, can be selected. The methods described herein can also be used to assess pharmacological selectivity and specificity, and toxicity.

Bioavailability and Toxicology of Candidate Modulators

Once identified, candidate modulators can be evaluated for bioavailability and toxicological effects using known methods (see, Lu, *Basic Toxicology, Fundamentals, Target Organs, and Risk Assessment,* Hemisphere Publishing Corp., Washington (1985); U.S. Pat. No. 5,196,313 to Culbreth (issued Mar. 23, 1993) and U.S. Pat. No. 5,567,952 to Benet (issued Oct. 22, 1996). For example, toxicology of a candidate modulator can be established by determining in vitro toxicity towards a cell line, such as a mammalian i.e. human, cell line. Candidate modulators can be treated with, for example, tissue extracts, such as preparations of liver, such as microsomal preparations, to determine increased or decreased toxicological properties of the chemical after being metabolized by a whole organism. The results of these types of studies are often predictive of toxicological properties of chemicals in animals, such as mammals, including humans.

Such bioavailability and toxicological methods can be performed using the methods, preferable using the screening systems of the present invention. Such methods include contacting a sample having a target with at least one photon producing agent, at least one photon reducing agent, and a test chemical. An optical signal from said at least one photon producing agent is detected, wherein said optical signal is related to a toxicological activity. Bioavailability is any known in the art and can be detected, for example by measuring reporter genes that are activated during bioavailability criteria. Toxicological activity is any known in the art, such as apoptosis, cell lysis, crenation, cell death and the like. The toxicological activity can be measured using reporter genes that are activated during toxicological activity or by cell lysis (see WO 98/13353, published Apr. 2, 1998). Preferred reporter genes produce a fluorescent or luminescent translational product (such as, for example, a Green Fluorescent Protein (see, for example, U.S. Pat. No. 5,625,048 to Tsien et al., issued Apr. 29, 1998; U.S. Pat. No. 5,777,079 to Tsien et al., issued Jul. 7, 1998; WO 96/23810 to Tsien, published Aug. 8, 1996; WO 97/28261, published Aug. 7, 1997; PCT/US97/12410, filed Jul. 16, 1997; PCT/US97/14595, filed Aug. 15, 1997)) or a translational product that can produce a fluorescent or luminescent product (such as, for example, beta-lactamase (see, for example, U.S. Pat. No. 5,741,657 to Tsien, issued Apr. 21, 1998, and WO 96/30540, published Oct. 3, 1996)), such as an enzymatic degradation product. Cell lysis can be detected in the present invention as a reduction in a fluorescence signal from at least one photon producing agent within a cell in the presence of at least one photon reducing agent. Such toxicological determinations can be made using prokaryotic or eukaryotic cells, optionally using toxicological profiling, such as described in PCT/US94/00583, filed Jan. 21, 1994, German Patent No 69406772.5-08, issued Nov. 25, 1997; EPC 0680517, issued Nov. 12, 1994; U.S. Pat. No. 5,589,337, issued Dec. 31, 1996; EPO 651825, issued Jan. 14, 1998; and U.S. Pat. No. 5,585,232, issued Dec. 17, 1996).

Alternatively, or in addition to these in vitro studies, the bioavailability and toxicological properties of a candidate modulator in an animal model, such as mice, rats, rabbits, or monkeys, can be determined using established methods (see, Lu, supra (1985); and Creasey, *Drug Disposition in Humans, The Basis of Clinical Pharmacology,* Oxford University Press, Oxford (1979), Osweiler, *Toxicology,* Williams and Wilkins, Baltimore, Md. (1995), Yang, *Toxicology of Chemical Mixtures; Case Studies, Mechanisms, and Novel Approaches,* Academic Press, Inc., San Diego, Calif. (1994), Burrell et al., *Toxicology of the Immune System; A Human Approach,* Van Nostrand Reinhld, Co. (1997), Niesink et al., *Toxicology; Principles and Applications,* CRC Press, Boca Raton, Fla. (1996)). Depending on the toxicity, target organ, tissue, locus, and presumptive mechanism of the candidate modulator, the skilled artisan would not be burdened to determine appropriate doses, $LD_{50}$ values, routes of administration, and regimes that would be appropriate to determine the toxicological properties of the candidate modulator. In addition to animal models, human clinical trials can be performed following established procedures, such as those set forth by the United States Food and Drug Administration (USFDA) or equivalents of other governments. These toxicity studies provide the basis for determining the efficacy of a candidate modulator in vivo.

Efficacy of Candidate Modulators

Efficacy of a candidate modulator can be established using several art recognized methods, such as in vitro methods, animal models, or human clinical trials (see, Creasey, supra (1979)). Recognized in vitro models exist for several diseases or conditions. For example, the ability of a chemical to extend the life-span of HIV-infected cells in vitro is recognized as an acceptable model to identify chemicals expected to be efficacious to treat HIV infection or AIDS (see, Daluge et al., *Antimicro. Agents Chemother.* 41:1082–1093 (1995)). Furthermore, the ability of cyclosporin A (CsA) to prevent proliferation of T-cells in vitro has been established as an acceptable model to identify chemicals expected to be efficacious as immunosuppressants (see, Suthanthiran et al., supra, (1996)). For nearly every class of therapeutic, disease, or condition, an acceptable in vitro or animal model is available. Such models exist, for example, for gastro-intestinal disorders, cancers, cardiology, neurobiology, and immunology. In addition, these in vitro methods can use tissue extracts, such as preparations of liver, such as microsomal preparations, to provide a reliable indication of the effects of metabolism on the candidate modulator. Similarly, acceptable animal models may be used to establish efficacy of chemicals to treat various diseases or conditions. For example, the rabbit knee is an accepted model for testing chemicals for efficacy in treating arthritis (see, Shaw and Lacy, *J. Bone Joint Surg. (Br)* 55:197–205 (1973)). Hydrocortisone, which is approved for use in humans to treat arthritis, is efficacious in this model which confirms the validity of this model (see, McDonough, *Phys. Ther.* 62:835–839 (1982)). When choosing an appropriate model to determine efficacy of a candidate modulator, the skilled artisan can be guided by the state of the art to choose an appropriate model, dose, and route of administration, regime, and endpoint and as such would not be unduly burdened.

In addition to animal models, human clinical trials can be used to determine the efficacy of a candidate modulator in humans. The USFDA, or equivalent governmental agencies, have established procedures for such studies (see www.fda.gov).

Selectivity of Candidate Modulators

The in vitro and in vivo methods described above also establish the selectivity of a candidate modulator. It is recognized that chemicals can modulate a wide variety of biological processes or be selective. Panels of cells based on the present invention can be used to determine the specificity of the candidate modulator. Selectivity is evident, for example, in the field of chemotherapy, where the selectivity of a chemical to be toxic towards cancerous cells, but not towards non-cancerous cells, is obviously desirable. Selective modulators are preferable because they have fewer side effects in the clinical setting. The selectivity of a candidate modulator can be established in vitro by testing the toxicity and effect of a candidate modulator on a plurality of cell lines that exhibit a variety of cellular pathways and sensitivities. The data obtained from these in vitro toxicity studies can be extended animal model studies, including human clinical trials, to determine toxicity, efficacy, and selectivity of the candidate modulator.

Identified Compositions

The invention includes compositions such as novel chemicals, and therapeutics identified as having activity by the operation of methods, systems or components described herein. Novel chemicals, as used herein, do not include chemicals already publicly known in the art as of the filing date of this application. Typically, a chemical would be identified as having activity from using the invention and then its structure revealed from a proprietary database of chemical structures or determined using analytical techniques such as mass spectroscopy.

One embodiment of the invention is a chemical with useful activity, comprising a chemical identified by the method described above. Such compositions include small organic molecules, nucleic acids, peptides and other molecules readily synthesized by techniques available in the art and developed in the future. For example, the following combinatorial compounds are suitable for screening: peptoids (PCT Publication No. WO 91/19735, Dec. 26, 1991), encoded peptides (PCT Publication No. WO 93/20242, Oct. 14, 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. USA 90: 6909–6913 (1993)), vinylogous polypeptides (Hagihara et al., J. Amer. Chem. Soc. 114: 6568 (1992)), nonpeptidal peptidomimetics with a Beta-D-Glucose scaffolding (Hirschmann, R. et al., J. Amer. Chem. Soc. 114: 9217–9218 (1992)), analogous organic syntheses of small compound libraries (Chen, C. et al., J. Amer. Chem. Soc. 116:2661 (1994)), oligocarbamates (Cho, C. Y. et al., Science 261: 1303 (1993)), and/or peptidyl phosphonates (Campbell, D. A. et al., J. Org. Chem. 59: 658 (1994)). See, generally, Gordon, E. M. et al., J. Med Chem. 37: 1385 (1994). The contents of all of the aforementioned publications are incorporated herein by reference.

The present invention also encompasses the identified chemicals and their respective compositions, typically in a pharmaceutical composition of the present invention that comprise a pharmaceutically acceptable carrier prepared for storage and subsequent administration, which have the pharmaceutically effective amount of the products disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

The compositions of the present invention may be formulated and used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the invention, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage for the products of the present invention can range broadly depending upon the desired affects and the therapeutic indication. Typically, dosages may be between about 10 kg/kg and 100 mg/kg body weight, preferably between about 100 μg/kg and 10 mg/kg body weight. Administration is preferably oral on a daily basis.

The exact formulation, route of administration and dosage can be chosen by the individual physician in view of the patient's condition. (See e.g., Fingl et al., in The Pharmacological Basis of Therapeutics, 1975). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, 18th Ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping, or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dye-stuffs or pigments may be added to the tablets or dragee coatings for identification or to characterize different combinations of active compound doses. Such formulations can be made using methods known in the art (see, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations).

EXAMPLES

The structure of CCF2/AM used in the experiments described herein is:

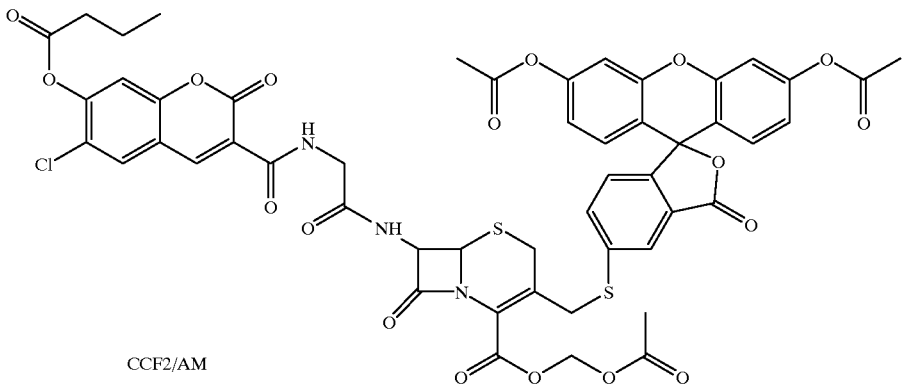

CCF2/AM

Example 1
Reduction of Solution Fluorescence

To investigate the ability of a photon reducing agent to reduce fluorescence of a solution, emission of a fluorophore from a sample was monitored in the presence and absence of a photon reducing agent. The following experiments show that photon reducing agents can be used to reduce solution based fluorescence from a fluorophore.

Fluorescence from a solution of a blue fluorescent dye, 6-chloro-7-hydroxy coumarin 3-carboxylate, was determined in the presence and absence of a 1 mM phenol red as the photon reducing agent. A solution of 0.5 $\mu$M 6-chloro-7-hydroxy coumarin-3-carboxylate in solvent containing 50% (vol/vol) aqueous 39 mM phosphate buffer pH 7.5 and 50% (vol/vol) methanol was prepared. After taking a front face fluorescence spectrum of this solution on a Spex Fluorolog 2, 1% (vol/vol) of a 100 mM aqueous Phenol Red stock solution was added and another spectrum taken. Front face fluorescence refers to exciting the sample at a right angle to the sample surface and collecting emitted light (for example, from the excited region or emission region) at 12.5 degrees from such angle of excitation.

Figure 2:
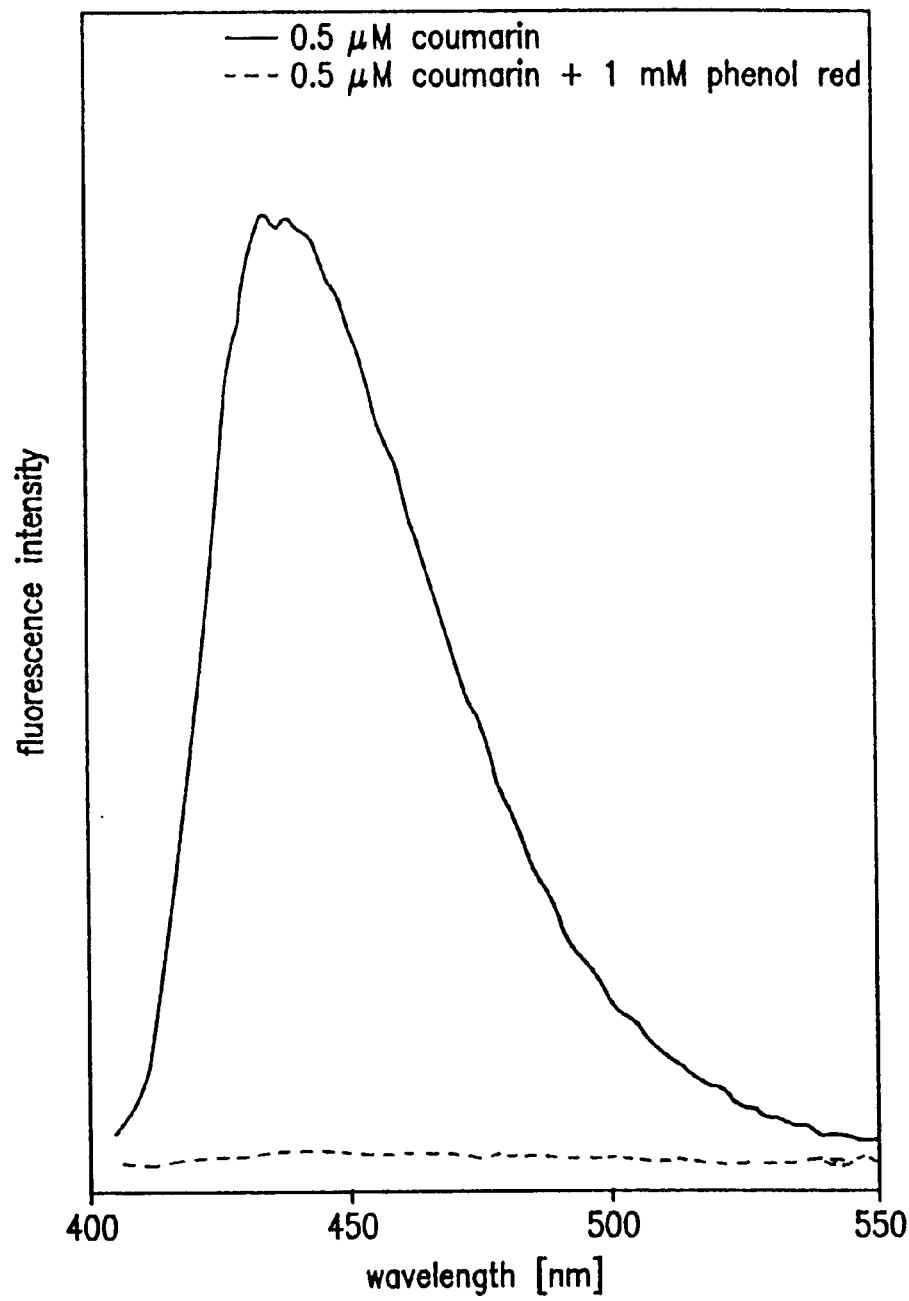
FIG. 2 shows the ability of phenol red to reduce the emission of fluorescence from a solution containing coumarin.

FIG. 2 shows these spectra. Addition of phenol red reduced front face fluorescence 70 fold. The photon reducing agent, phenol red, substantially reduced the solution based fluorescence signal. Although the inventors do not wish to be bound by any proposed mechanism, at 50% (vol/vol), the organic solvent (methanol) in the solution may prevent association of the dye molecules in solution. This is consistent with the explanation that fluorescence reduction does not require ground-state fluorescence quenching due to dye stacking. This result is consistent with a photon reducing agent decreasing fluorescence of the fluorophore by absorbing the excitation or emission light to or from the fluorophore or by accepting the energy of the excited singlet state of the fluorophore (a state that gives rise to the fluorescence) by a long-range energy transfer mechanism, such as fluorescence resonance energy transfer.

Example 2
Reduction of Solution Fluorescence is not Necessarily Associated with Stacking To further investigate the ability of a photon reducing agent to reduce fluorescence of a solution, fluorescence of a dye in the presence of a photon reducing agent was monitored in the presence and absence of methanol. The following experiment shows that a photon reducing agent, phenol red, can be used to reduce fluorescence from a fluorophore in aqueous solution without dye stacking.

The fluorescence from a fluorophore in the presence of a photon reducing agent (phenol red) was determined in both aqueous buffer and aqueous buffer containing 50% (vol/vol) methanol. A 10 $\mu$M solution of 6-chloro-7-hydroxy coumarin-3-carboxylate was prepared in 39 mM phosphate buffer pH 7.5 and in a 1:1 mixture of same phosphate buffer and methanol. 1% (vol/vol) of a 100 mM aqueous Phenol Red stock solution was added to the solutions.

Figure 3:
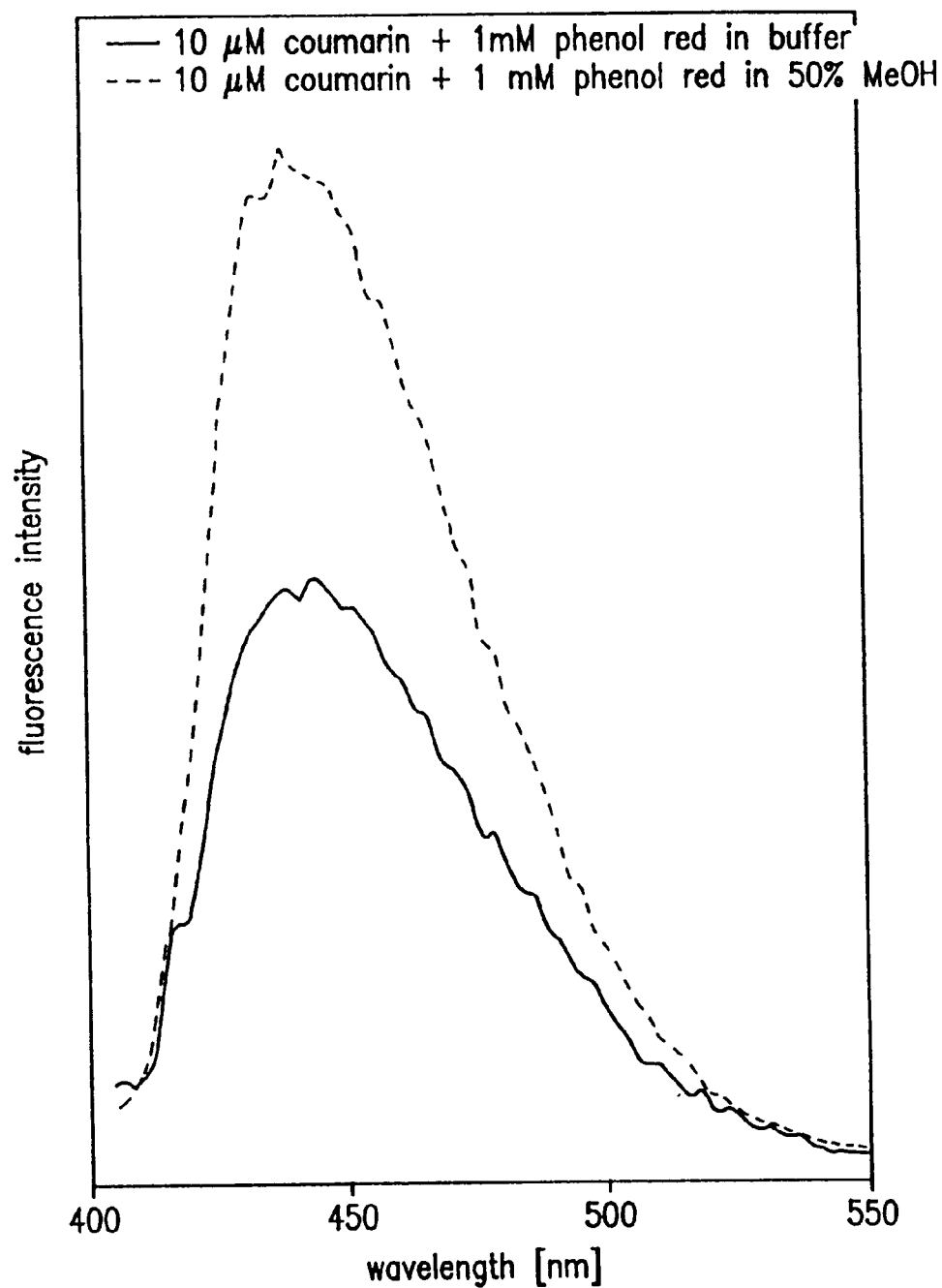
FIG. 3 shows the ability of phenol red to reduce the emission of fluorescence from a solution containing coumarin the presence and absence of methanol.

FIG. 3 shows front-face fluorescence spectra of these solutions were obtained on a Spex Fluorolog 2. The presence of methanol increased fluorescence compared to an all aqueous buffer. These results further confirm that the fluorescence decrease observed in Example 1 was not entirely due to dye stacking. Note the relative fluorescence in Example 2 is comparable or less than the fluorescence of coumarin/phenol red sample of Example 1.

The increased fluorescence in the presence of methanol in the buffer is consistent with finding that 50% methanol buffer increased 6-chloro-7-hydroxy coumarin-3-carboxylate fluorescence in the absence of a photon reducing agent by about 30 percent. The increased fluorescence in the presence of methanol in the buffer is also consistent with finding that the 50% methanol buffer decreased the absorbance of the photon reducing agent phenol red at the emission wavelength of the coumarin by about 20 percent. Under these conditions, stacking of the dye-based photon reducing agent and the photon producing agent does not contribute significantly to fluorescence-reduction effect of dye-based photon reducing agents. Dye stacking is especially unlikely when the fluorophore is very water soluble and small, such as 6-chloro-7-hydroxy coumarin-3-carboxylate.

Example 3
Test of Reduction of Solution Fluorescence Using Non-dye Quenchers and Particulates To investigate the ability of a candidate photon reducing agent to reduce fluorescence of a solution, fluorescence of a fluorophore in the presence of a candidate photon reducing agent was monitored as a function of photon reducing agent concentration. The candidate photon reducing agents used were non-dye molecules and particulates. The following experiments show that non-dye molecules and particulates can be used as photon reducing agents to reduce fluorescence from a fluorophore in aqueous buffer.

Signals from fluorescent dye solutions containing no photon reducing agents or photon reducing agents, such as Schilling Red (water, propylene glycol, FD&C Red No. 40 (Allura red), FD&C Red No. 3 and propyparaben (McCormick & Co., Inc. Hunt Valley, Md.) and phenol red, were compared to solutions containing candidate photon reducing agents, non-dye molecules (diatrizoic acid and Tris(2-amino ethyl)amine) and particulate ink (Higgins ink). In a 96 well microtiter plate, two fold serial dilutions of aqueous 0.5 M diatrizoic acid and 1 M tris(2-aminoethyl) amine (adjusted to pH 7.5 with hydrochloric acid), 100 mM phenol red, Schilling Red food dye and Higgins ink were prepared in the presence of 10 µM 6-chloro-7-hydroxy coumarin-3-carboxylate in the 39 mM phosphate buffer (pH 7.5). The well volume was 100 µl. A two-fold serial dilution of 10 µM 6-chloro-7-hydroxy coumarin-3-carboxylate in phosphate buffer pH 7.5 was prepared for comparison. A linear signal was shown over the range of coumarin concentrations tested. The fluorescence emission intensity of the samples was measured on a Cytofluor microtiter plate fluorimeter. The samples were excited with 395 nm light and fluorescence emission measured at 460 nm. Data for the Higgins ink and Schilling Red solutions were normalized by absorbance at 395 nm and 460 nm to the phenol red solution because their concentrations were either unknown (Schilling Red) or not defined (Higgins ink).

Figure 4:
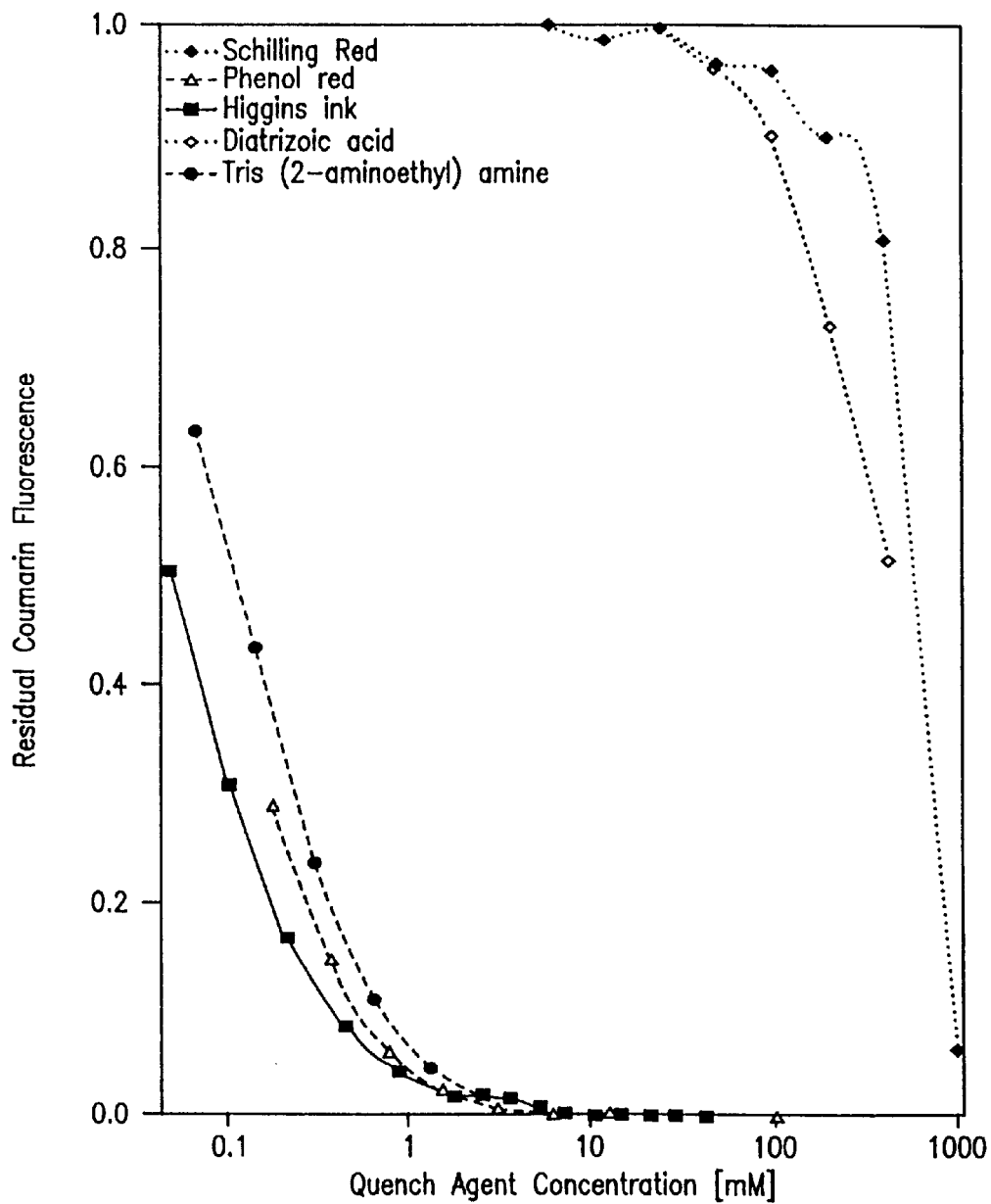
FIG. 4 shows the dependence of emission of fluorescence from a solution on candidate photon reducing agent concentration.

FIG. 4 graphs the concentration of the candidate photon reducing agent against the residual coumarin fluorescence, which shows the dependence of sample fluorescence on candidate photon reducing agent concentration. Efficient reduction of fluorescence occurs at non-dye concentrations greater than 0.5 M, while the particulate Higgins ink and Schilling Red were similarly effective to phenol red. This result demonstrates that photon reducing agents that act as only as collisional quenchers (diatrizoic acid and tris(2-aminoethyl)amine) will typically require concentrations higher than 100 mM, which could contribute to ionic strength effects in potential assays. These results also demonstrate that a photon reducing agent consisting of light-absorbing (or light scattering) particulate matter, such as an ink, can effectively reduce solution fluorescence.

Example 4

Test of Reduction of Solution Fluorescence Using Dye-Based Photon Reducing Agents with Absorbance Spectra Sufficiently Overlapping with the Emission or Excitation Spectrum of the Photon Producing Agent To investigate the ability of a candidate dye-based photon reducing agent to reduce fluorescence of a solution, fluorescence of a fluorophore in the presence of a candidate photon reducing agent was monitored as a function of the photon reducing agent concentration. The candidate photon reducing agents were dye molecules with different absorption spectra compared to three different fluorophores. The following experiments demonstrate that dye based photon reducing agents are most effective in reducing solution based fluorescence when their absorption maxima significantly overlaps the excitation and emission spectra of the fluorophore.

The efficiency with which water soluble dyes (photon reducing agents) of different colors were able to reduce fluorescence from fluorophore solutions of 7-hydroxycoumarin, CCF2, fluorescein and rhodamine B was studied. A mixture of dye photon reducing agents with high extinction over the range from 380–555 nm (named Tararaf) was also studied.

TABLE 1

Absorption maxima of dyes

| Naphthol Yellow: | 428 (392) nm |
| Tartrazine: | 425 nm |
| Phenol Red: | 557 (423) nm |
| Acid Red 37: | 513 nm |
| Acid Fuchsin: | 546 nm |
| Trypan Blue: | 607 nm |
| Patent Blue: | 635 nm |
| Tararaf: | 441 (513) nm |

(Tararaf contains Tartrazine, Acid Red 37 and Acid Fuchsin in a molar ratio of 5:6:4)

TABLE 2

Excitation and emission wavelength used in the study of fluorophores

| 6-Chloro-7-hydroxycoumarin-3-carboxylate: | ex. 395 nm, em. 460 nm |
| CCF2: | ex. 395 nm, em. 530 nm |
| Fluorescein: | ex. 485 nm, em. 530 nm |
| Rhodamine B: | ex. 530 nm, em. 595 nm |

The dye photon reducing agents were made 20 mM in 39 mM phosphate buffer pH 7.43 containing 10 µM of fluorescent dye. The Tararaf mixtures concentration was adjusted for its component Tartrazine to be 20 mM. In a 96-well fluorescence micro titer plate ten two-fold serial dilutions of these dyes were prepared with buffer containing 10 µM fluorescent dye. The fluorescence of the solutions in the wells was measured using a microtiter fluorimeter. The values were background subtracted and divided by the value obtained for 10 µM fluorescent dye in the absence of photon reducing agent. The values so obtained were termed residual fluorescence.

Figure 5:
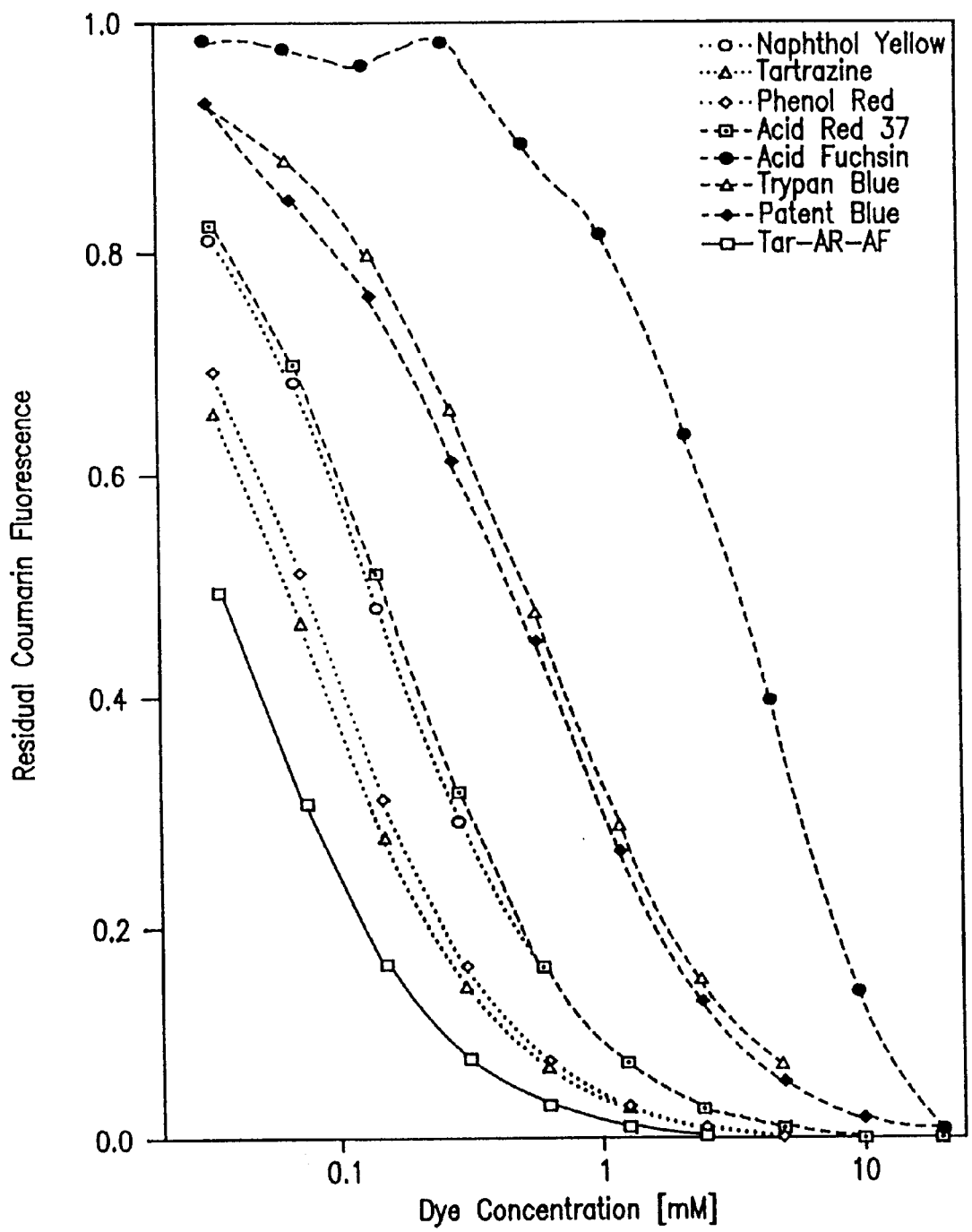
FIG. 5 shows the dependence of emission of fluorescence from a solution containing coumarin in the presence of various photon reducing agents.

FIG. 5 shows 6-chloro-7-hydroxycoumarin-3-carboxylate solution fluorescence as a function of colored photon reducing agent concentration. Single yellow dyes that absorb coumarin excitation and emission light reduced fluorescence at lower concentrations better than single red or blue dyes. Tararaf also effectively reduced solution fluorescence. The absorbance spectra of the components of Tararaf significantly overlap with the excitation and emission spectra of this fluorophore.

Figure 6:
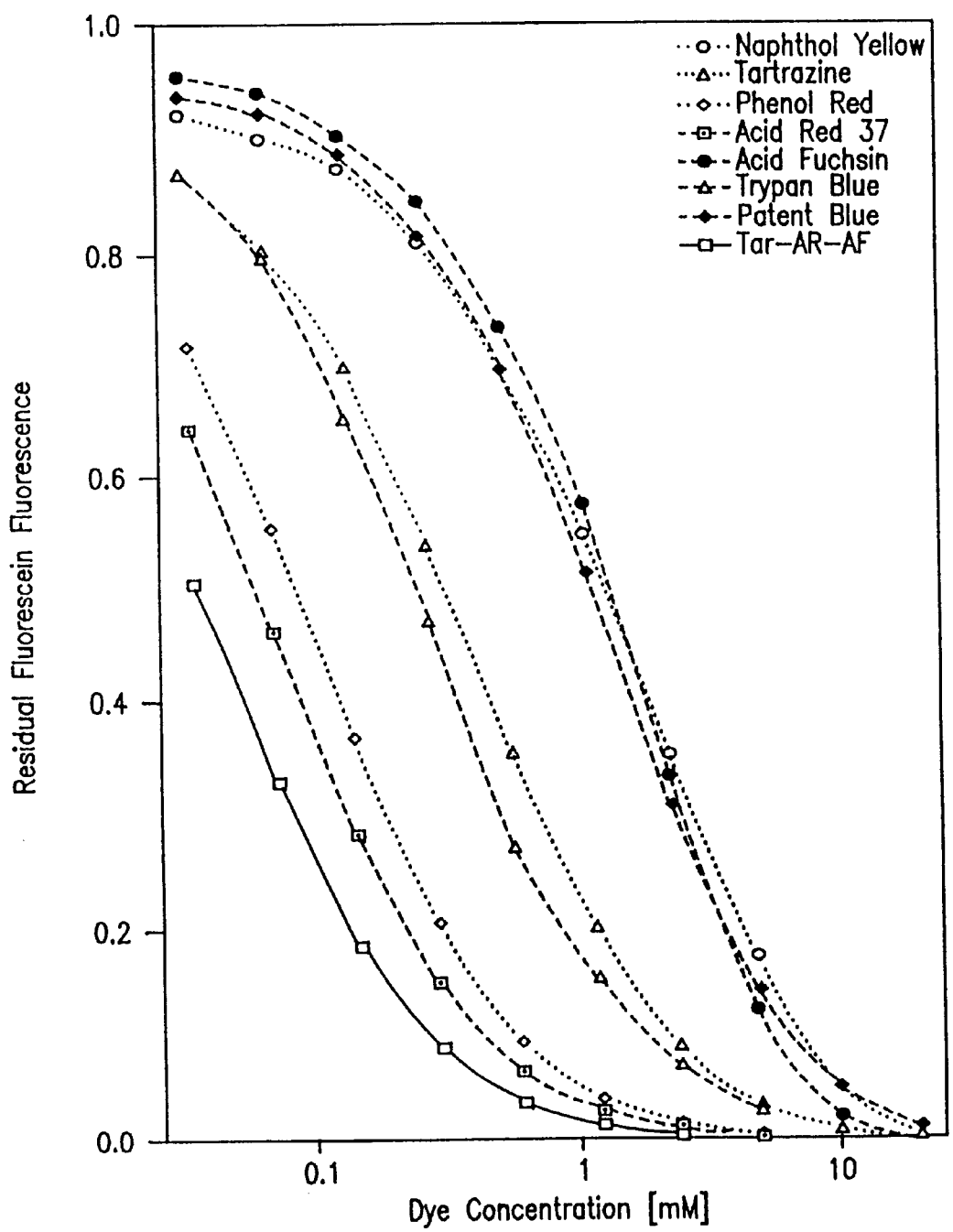
FIG. 6 shows the dependence of emission of fluorescence from a solution containing fluorescein in the presence of various colored photon reducing agents.

FIG. 6 shows fluorescein solution fluorescence as a function of colored photon reducing agent concentration. Single yellow and red dyes that absorb in the excitation and/or emission spectra of fluorescein reduced solution fluorescence at lower concentrations better than blue dyes that absorb predominantly outside that range of wavelengths. Tararaf also effectively reduced solution fluorescence. The absorbance spectra of the components of Tararaf significantly overlap with the excitation and emission spectra of this fluorophore.

Figure 7:
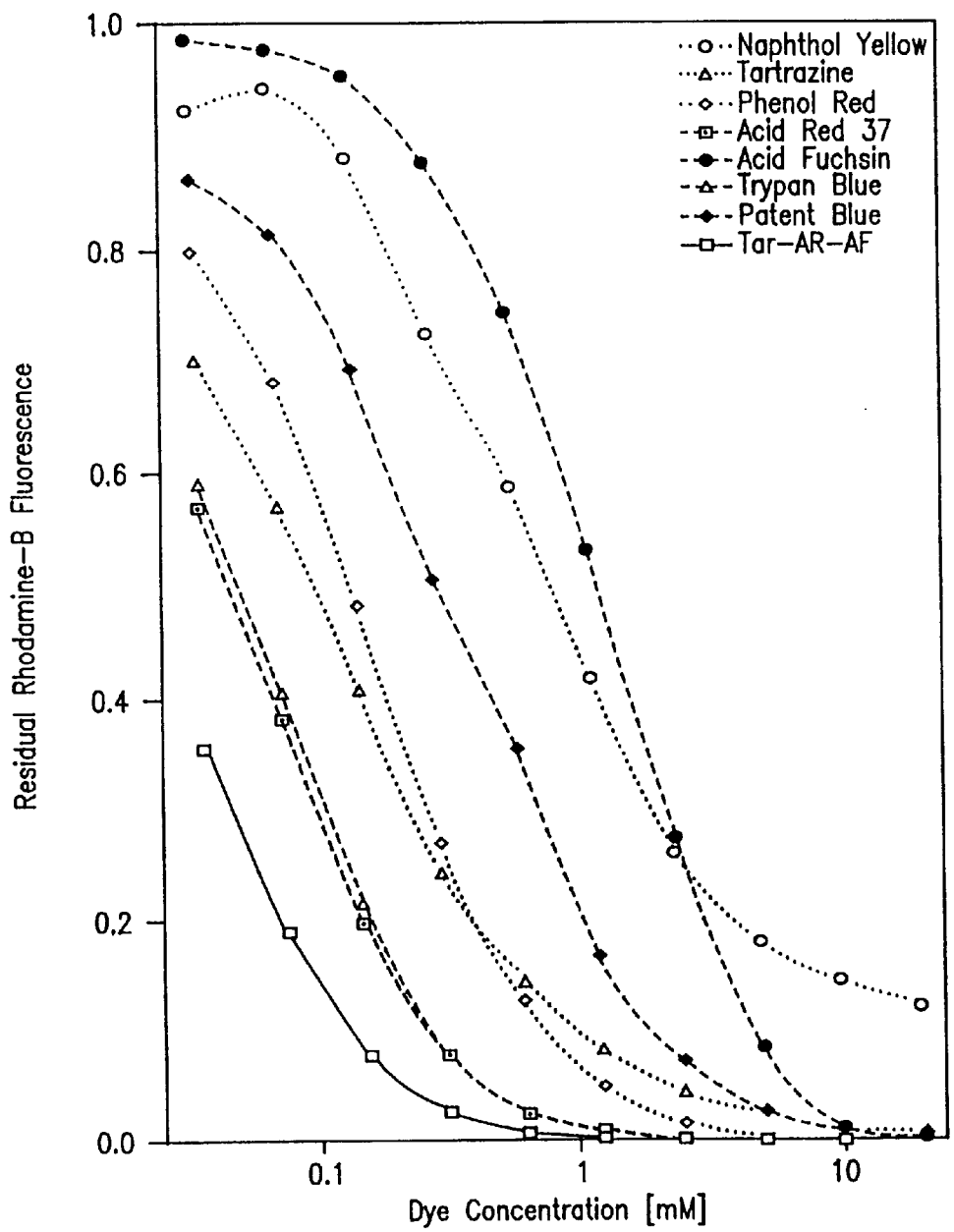
FIG. 7 shows the dependence of emission of fluorescence from a solution containing rhodamine in the presence of various colored photon reducing agents.

FIG. 7 shows rhodamine solution fluorescence as a function of colored photon reducing agent concentration. Red dyes that absorb in excitation spectrum of rhodamine and blue dyes that absorb in the emission spectrum of rhodamine reduced solution fluorescence at lower concentrations more than yellow dyes that absorb outside that range of wavelengths. Tararaf effectively reduced solution fluorescence. The absorbance spectra of the components of Tararaf significantly overlap with the excitation spectrum of this fluorophore.

Figure 8:
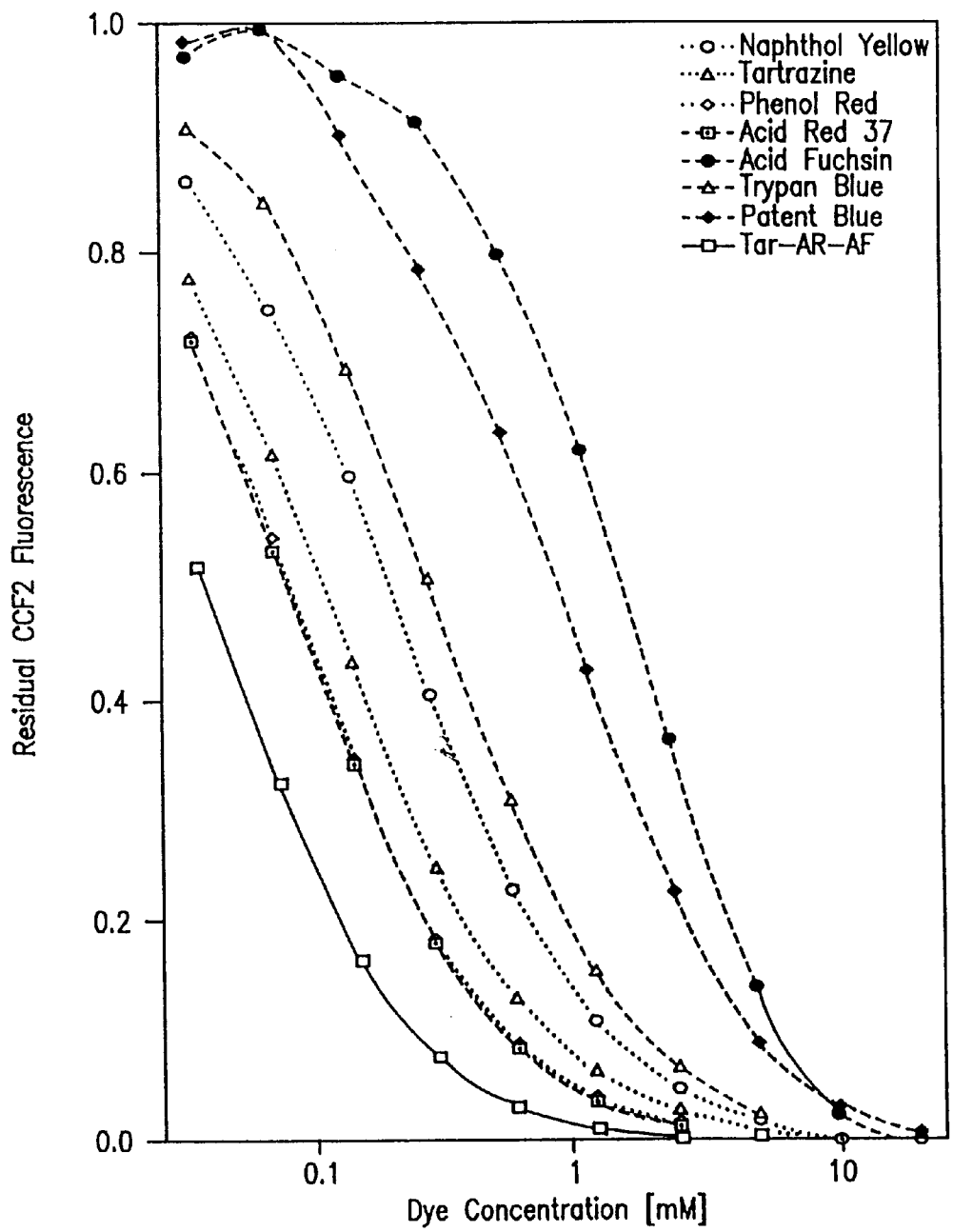
FIG. 8 shows residual CCF2 solution fluorescence as a function of colored photon reducing agent concentration.

FIG. 8 shows residual CCF2 solution fluorescence as a function of colored photon reducing agent concentration. Single yellow and red dyes that absorb in the excitation and/or emission spectra of CCF2 reduced fluorescence at lower concentrations than blue dyes that absorb outside that range. Tararaf also effectively reduced solution fluorescence. The absorbance spectra of the components of Tararaf significantly overlap with the excitation and emission spectra of this fluorophore.

These experiments demonstrate that dye-based photon reducing agents are most effective in reducing solution based fluorescence when their absorption maxima lie in the spectral range of the excitation and/or emission of the fluorophore.

Example 5
Test of Reduction of Solution Fluorescence Using Non-dye Based Photon Reducing Agents that Electronically Interact with the Photon Producing Agent To investigate the ability of a candidate transition metal based or transition metal complex based photon reducing agents to reduce fluorescence emitted from a solution, fluorescence of a fluorophore in the presence of a candidate photon reducing agent was monitored as a function of photon reducing agent concentration. The candidate photon reducing agents used were ions that can potentially electronically interact with a fluorophore. The following experiments demonstrate that non-dye based photon reducing agents that are transition metal based or transition metal complexes can be easily tested and selected to reduce solution based fluorescence of a particular fluorophore. The following experiments demonstrate that salts of transition metals and their complexes can act as photon reducing agents of specific fluorophores.

Figure 9A:
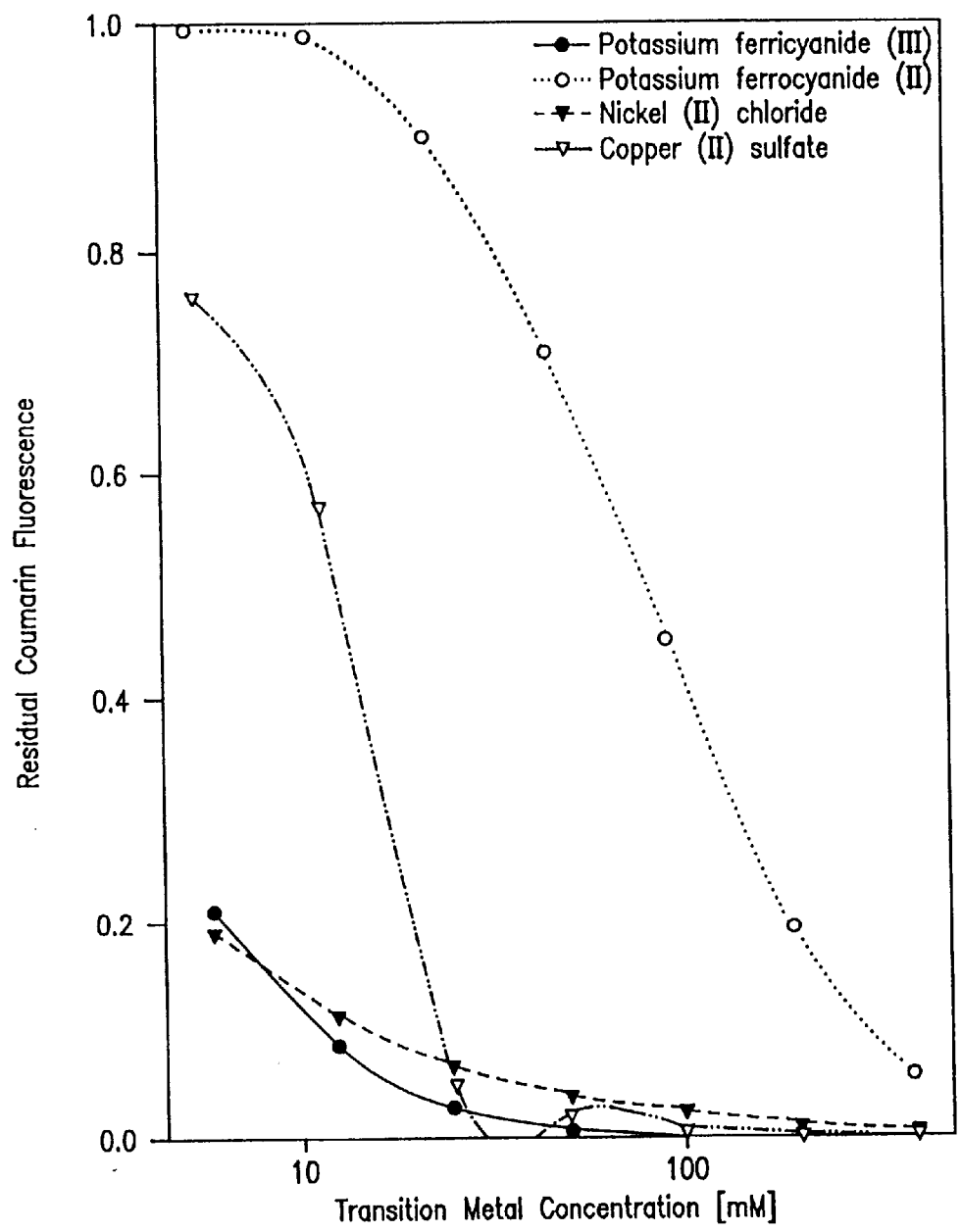
FIG. 9A, FIG. 9B, and FIG. 9C show the reduction of solution fluorescence using non-dye based photon agents that electronically interact with a photon producing agent.
Figure 9B:
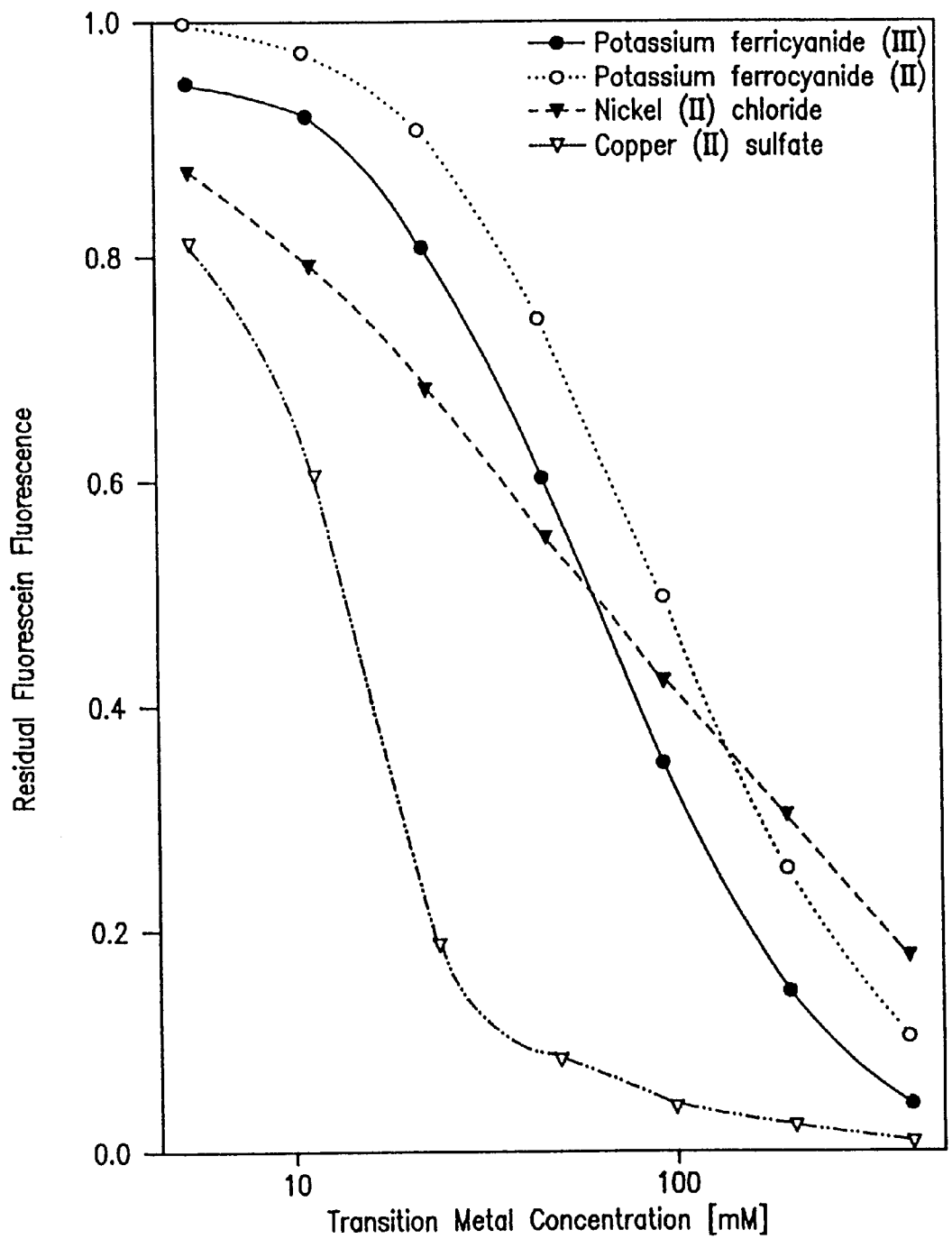
Figure 9C:
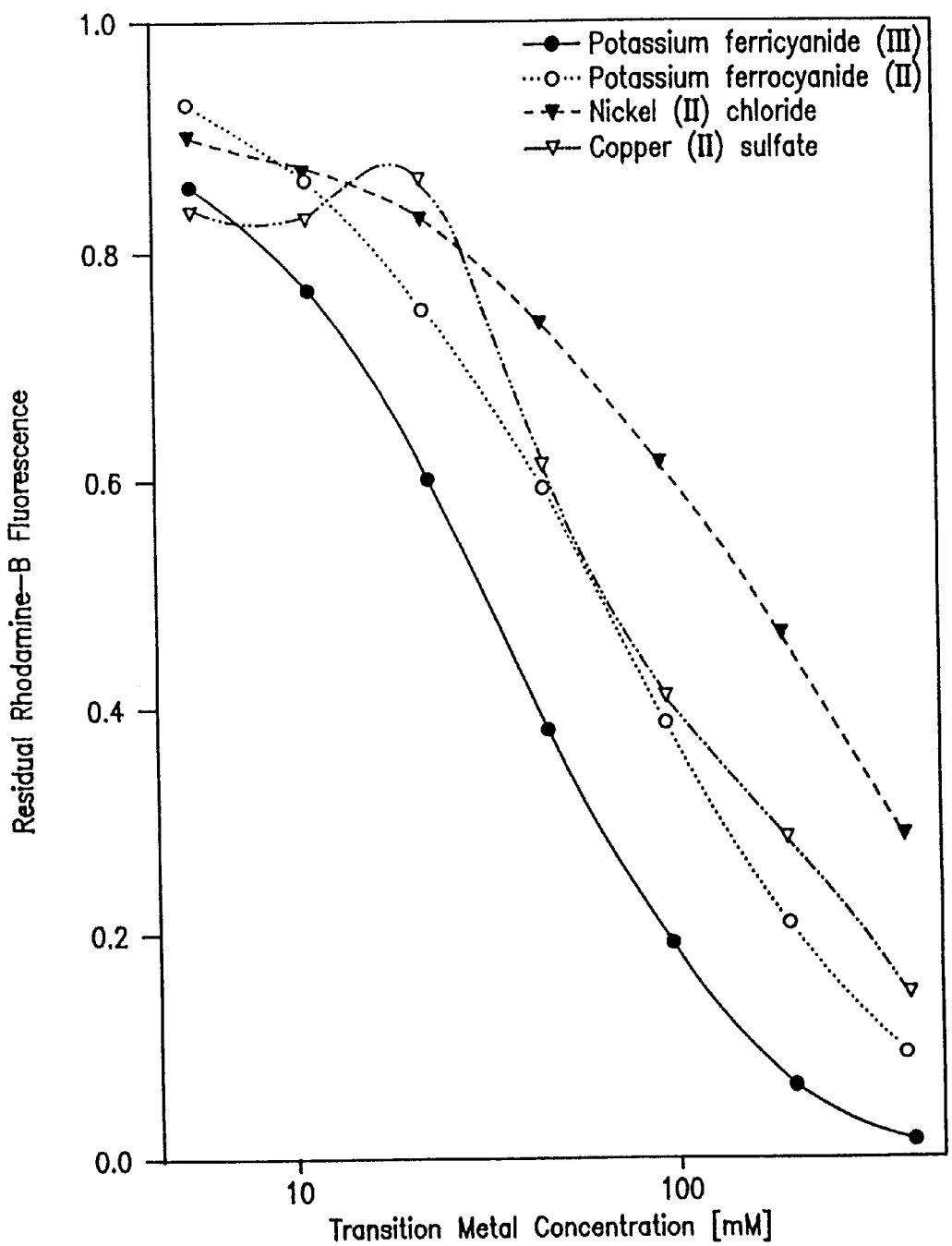

Fluorescence was measured with a microtiter plate fluorimeter with excitation at 395 nm and emission at 460 nm for the coumarin fluorophore, excitation 485 nm and emission at 530 nm for fluorescein and excitation 530 nm and emission at 590 nm for rhodamine B. 500 mM solutions of potassium ferrocyanide (II), potassium ferricyanide (III), nickel (II) chloride and copper (II) sulfate were prepared in water. 800 $\mu$l of each stock solution was diluted with 190 $\mu$l 50 mM K-MOPS pH 7.15 and 10 $\mu$l 1 mM fluorophore solution to a final 400 mM (stock solution). Two-fold serial dilutions of these stock solutions into 10 $\mu$M fluorophore containing K-MOPS buffer were prepared in 96 well black (clear bottom) Costar plates. As in Example 4, the measured values were background subtracted and normalized to values obtained from fluorophore in absence of photon reducing agents (see FIG. 9).

These experiments demonstrated that fluorescence from coumarin fluorophores can be reduced by iron (III) and nickel (II) salts in the low millimolar range. Other ions fluorophore combinations demonstrated an affect at higher concentrations (approximately 10 mM and above).

Example 6
Test of Reduction of Solution Fluorescence as s Function of Path Length To further investigate the ability of photon reducing agents to reduce fluorescence emitted from a solution, fluorescence emitted from a solution containing a fluorophore in the presence of a photon reducing agent was monitored as a function sample thickness. The following experiments surprisingly demonstrate that dye-based photon reducing agents reduce solution fluorescence of a fluorophore at short transmission distances.

A photon reducing agent, phenol red, was tested with a fluorophore, coumarin, as a function of sample thickness (path length). The experiment was conducted using a microscope equipped with epifluorescence. The liquid samples were drawn into low fluorescence capillary tubes of fixed path length (Vitro Dynamics, Rockaway N.J.) as indicated in the graphs. The following samples were evaluated:

1) 10 $\mu$M coumarin (diamonds)
2) 10 $\mu$M coumarin+1 mM phenol red (squares)
3) 10 $\mu$M coumarin+5% (vol/vol) Schilling Red (triangles).

The samples were excited using a 405/20 filter via a 425 dichroic reflector through a 20× objective (Zeiss 20×Fluar). Emitted light was filtered through a 460/50 filter and detected by an intensified CCD camera (Stanford Photonics, Menlo Park, Calif.). The detector output was converted to a 512×512 pixel eight-bit digital image. The data reflect the average intensity within a 20×20 pixel area within the capillary. The background intensity of the field was subtracted from all values.

Figure 10A:
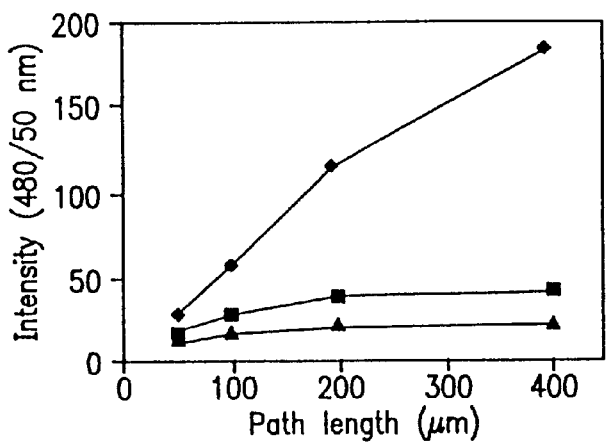
FIG. 10A, FIG. 10B, and FIG. 10C show coumarin fluorescence is attenuated by phenol red at various pathlengths.

FIG. 10A shows the raw data for this experiment. Coumarin fluorescence was significantly attenuated by the presence of the phenol red. Longer paths are also increasingly attenuated.

Figure 10B:
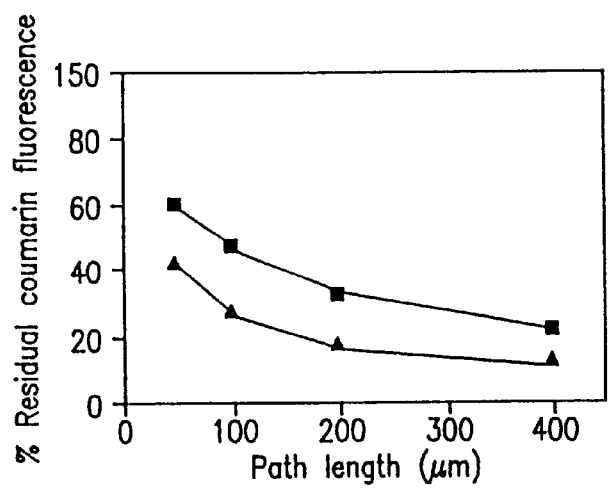

FIG. 10B shows the percentage of coumarin fluorescence observed as a function of path length for each of the dyes tested. The decrease of fluorescence at short pathlengths is not consistent with a filtering affect of the photon reducing agent. At short pathlengths and low concentrations of a photon reducing agent there is not a sufficient number of photon reducing agent molecules to filter out light.

Figure 10C:
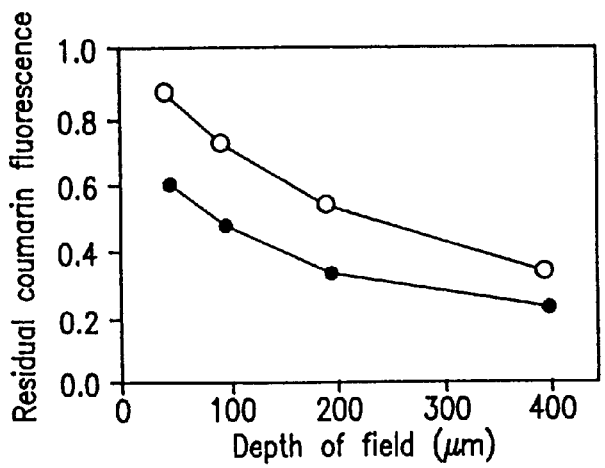

FIG. 10C shows the calculated decrease in coumarin fluorescence based on filtering affects. A Beer-Lambert relationship was used to model the expected decrease in fluorescence due to the effect of filtering light either by decreasing the amount of light available for excitation of the fluorophore or the amount of light emitted by the fluorophore.

These results demonstrate that photon reducing agents can be effective in reducing solution fluorescence in shallow samples, such as low volume assay samples. This is a surprising result because the amount of dye that is located in the space between the fluorophore and detector in this instance is quite small. This effect is consistent with deactivation of the excited fluorophore by fluorescence resonance energy transfer (FRET) to the photon reducing agents. The average distance between molecules in millimolar solutions of photon reducing agents is less than 100 Å. At such short distances FRET has been shown to be very efficient means of quenching fluorophore fluorescence. Although dye based photon reducing agents can reduce solution fluorescence at relatively short pathlengths, such photon reducing agents also allow nearly complete transmission (greater than about 80%) through shorter path lengths (e.g., less than 15 $\mu$m), which is appropriate for monitoring most mammalian cells.

Example 7
Photon Reducing Agents Reduce Undesired Fluorescence in Cell Based Assays To investigate the ability of photon reducing agents to reduce undesired fluorescence of a cell-based assay, fluorescence of a fluorophore in the presence of a photon reducing agent was monitored using mammalian cells. The following experiments surprisingly demonstrate that photon reducing agents reduce solution based fluorescence of a fluorophore in cell-based assays.

The fluorescence readout of CCF2 (a substrate for beta-lactamase) in the presence and in the absence of the photon reducing agents was measured. The derivative CCF2/AM, as described in PCT publication WO96/30540 (Tsien), is a vital dye that diffuses into cells and is trapped by living cells. Cells having esterase activity that cleaves ester groups on the CCF2/AM molecules, which results in a negatively charged molecule CCF2 that is trapped inside the cell. Trapped dye appears as green fluorescence L: inside of living cells devoid of beta-lactamase. Cells expressing beta-lactamase show blue fluorescence because the product of the beta-lactamase cleavage of CCF2 has blue fluorescence. CCF2 was incubated with Jurkat cells as previously described (see WO96/30540). These cells were not attached to the microtiter plates but are allowed to settle in the plate wells.

In these experiments, two sets of loading conditions (5 uM CCF2/AM lot#003 and 10 uM CCF2/AM lot#003) and two types of photon reducing agents (5% v/v Schilling Red Food Dye and 0.660 mM (final concentration) phenol red) were used. The presence of photon reducing agents increased the signal to noise ratio of the assay at least 200 to 300 percent compared to the absence of a photon reducing agent. Schilling Red Food Dye can vary from batch to batch. Thus, it is important to test each batch before using it in a large series of experiments or cell-based screens. In such cell-based assays solution fluorescence is typically from a fluorophore (such as CCF2/AM or its hydrolysis products) in the cell culture medium that baths the cells.

Beta-lactamase activity is preferably assessed by addition of $\frac{1}{6}^{th}$ volume CCF2/AM aqueous loading solution containing 6 $\mu$M CCF2/AM, 24% PEG-400, 6.2% DMSO, 0.6% Pluronic F127, 7.2 mM Tartrazine, 7.2 mM Acid Red 40 to microtiter wells at room temperature. After 30 min incubation, the fluorescence from the wells is read on a microtiter plate fluorimeter with excitation at 395/20 nm and emission at 460/40 nm and 530/30 nm. The raw fluorescence emission values were corrected for the signal from wells devoid of cells. Then, the corrected signal from the blue channel (460/40 nm) was divided by the signal from the green channel (530/30 nm). This type of analysis is referred to as ratioing. With the gain settings used for this experiment, a population of greater than 95% blue fluorescent cells (>95% cells expressing beta-lactamase) will give a ratio of greater than 3.0 and a population of entirely green fluorescent cells (no cell expressing any beta-lactamase) will give a ratio of about 0.1–0.2.

A comparison to prior art methods to reduce background fluorescence in cell-based assays was made. In the "washed assay" format, cells are stimulated to express beta-lactamase, washed, loaded with CCF2/AM, washed with CCF2/AM free media, and then plated out into micro-titer plates for fluorescence readout. Such a protocol with wash steps can work; however, the protocol has serious limitations and drawbacks for screening, high-throughput manipulations, and miniaturization. The washed format was compared with unwashed cells in the absence and presence of a photon reducing agent (Red Food Dye) at different concentrations ranging from 0 to 1.064 mM final using a fluorescence readout from a microtiter plate reader described herein. Photon reducing agents used in conjunction with the CCF2/AM substrate ester is often referred to as the "Enhanced Substrate System or ESS."

Figure 11:
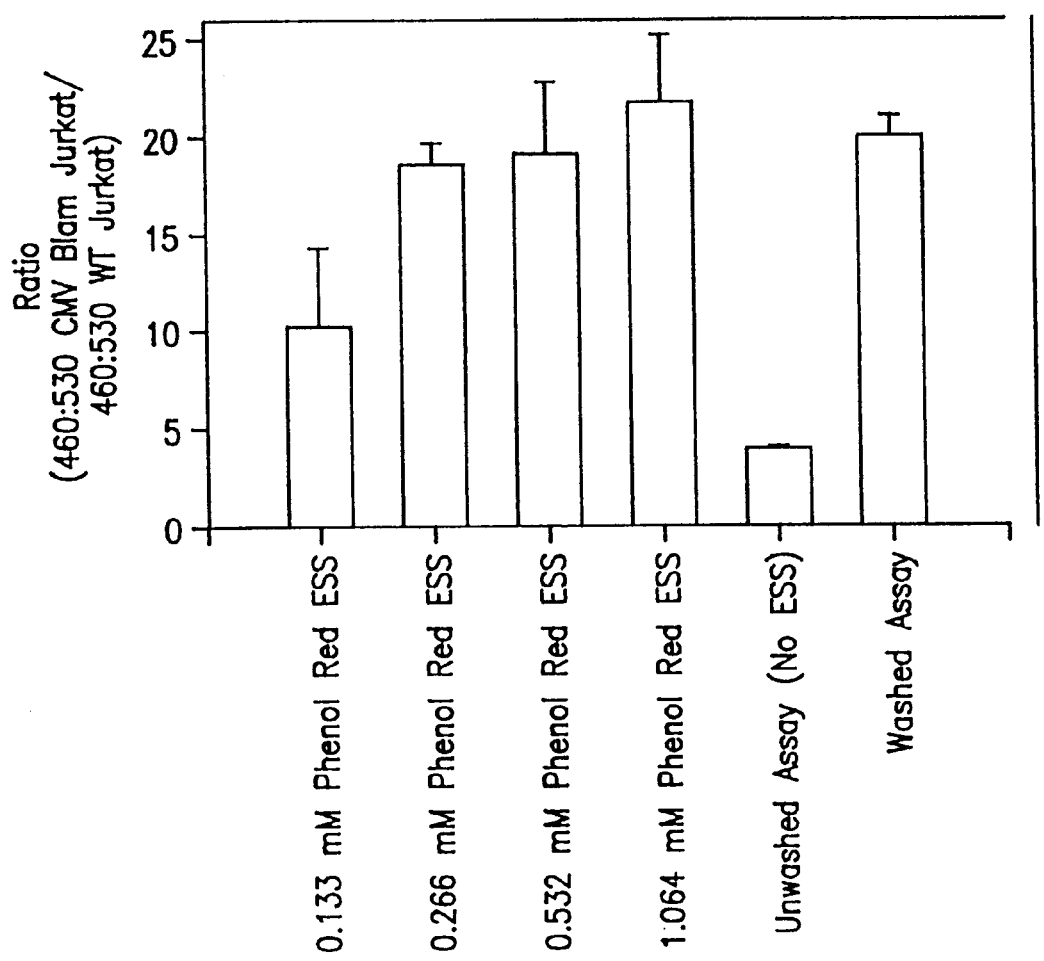
FIG. 11 shows that photon reducing agents reduce the fluorescence emission in unwashed cells and yields signals comparable to signals from washed cells.

FIG. 11 shows that photon reducing agents reduce fluorescence in unwashed cells and yields signals comparable to signals from washed cells. Photon reducing agents also provide much better signals than when no photon reducing agent is present. All data points are background (buffer plus ESS plus CCF2/AM (no cells)) subtracted. Data is typically expressed as the ratio of ratio. The first ratio is the ratio of fluorescence values at the two indicated emission wavelengths (460 nm/530 nm) for each experimental data point. The second ratio is the ratio of first ratio for the two experimental condition of cells constitutively expressing beta-lactamase and wildtype cells (CMV cells/wildtype cells).

Example 8
Testing of Dye-Based Photon Reducing Agents for Cytotoxicity in Cell Based Assays To investigate the ability of candidate dye-based photon reducing agents to reduce undesired fluorescence in a cell based assay, cytotoxicity in the presence of a candidate photon reducing agent was monitored as a function of the photon reducing agent concentration. The candidate photon reducing agents were selected from a number of dyes based on their absorbance spectra and use with living systems. The following experiments demonstrate that dye-based photon reducing agents can be easily tested and selected for their compatibility with cell-based assays.

From an initial list of 50 dye compounds, the following dyes were selected and tested with mammalian cells: Bromophenol Blue, Chlorophenol Red, Tartrazine, Phenol Red, Naphthol Yellow, Chromotrope F8, Chromazurol S, Patent Blue, Chromotrope 2R, Quinoline Yellow, Acid Fuchsin, Erythrosin, Acid Red 37, and Alizarin Red.

The toxicity of candidate dye-based photon reducing agents on mammalian cells was tested with wild-type Jurkat cells. Cells were incubated in microtiter plate assay wells at room temperature for 3 hours in the presence of different concentrations of candidate dye-based photon reducing agents. Propidium iodide was then added to all wells of the assay plate, and the percentage of dead cells in each well was estimated. Dead cells did not exclude propidium iodide.

Figure 12:
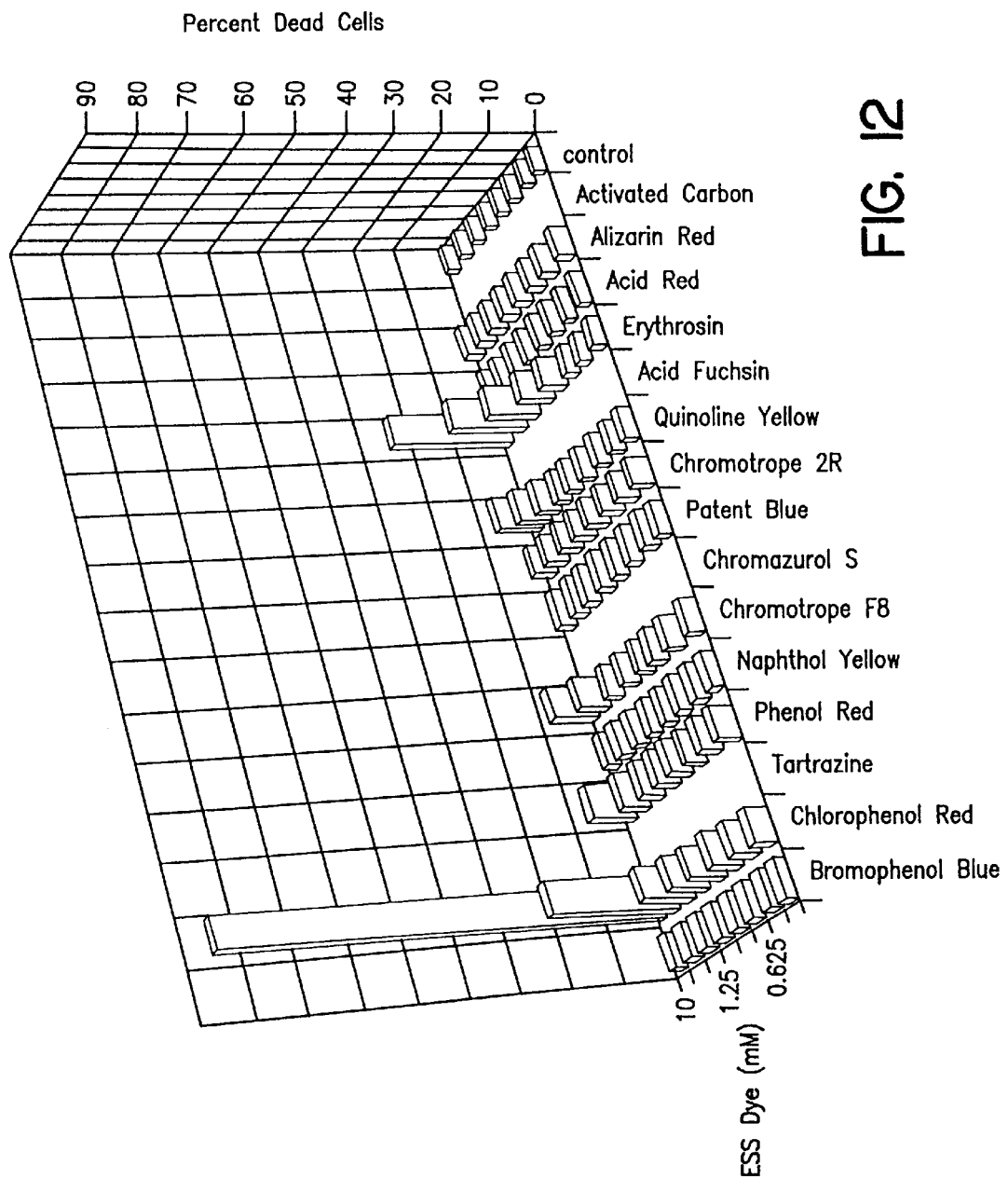
FIG. 12 summarizes the results of photon reducing agent toxicity testing.

FIG. 12 summarizes the results of candidate dye-based photon reducing agent toxicity testing. Over the concentrations tested only one candidate dye-based photon reducing agent showed significant cytotoxicity over a three hour time period. Presumably at shorter time periods, the candidate dye-based photon reducing agents will have even less of a cytotoxic effect.

Example 9
Testing of Dye-Based Photon Reducing Agents for Affects on Gene Activation and Intracellular Enzyme Activity in Cell Based Assays To further investigate the ability of candidate dye-based photon reducing agents to reduce undesired fluorescence in a cell-based assay, gene activation and intracellular enzyme activity in the presence of a candidate photon reducing agent was monitored as a function of the photon reducing agent concentration. The candidate photon reducing agents were selected from a number of dyes based on their absorbance spectra and use with living systems. The following experiments demonstrate that dye-based photon reducing agents can be easily tested and selected for their compatibility with cell-based assays having transcriptional activity.

Jurkat cells were treated as described herein for CCF2 experiments. The cells have a G-protein coupled receptor that can activate a response element controlling the transcription of beta-lactamase. Cells were stimulated with an agonist for the G-protein coupled receptor in the presence of different concentrations of individual candidate dye-based photon reducing agents that were preincubated with the cells. Cells were then incubated with CCF2/AM. Cells were subsequently evaluated for CCF2/AM loading, and conversion to CCF2, and for reporter gene expression using a microtiter plate fluorimeter. Immediately before fluorescence readout, the photon reducing agent, Schilling Red Food Dye, was added to all wells of the assay plate in order to normalize solution fluorescence. Thus, these experiments were designed to investigate cell function in the presence candidate photon reducing agents.

Figure 13:
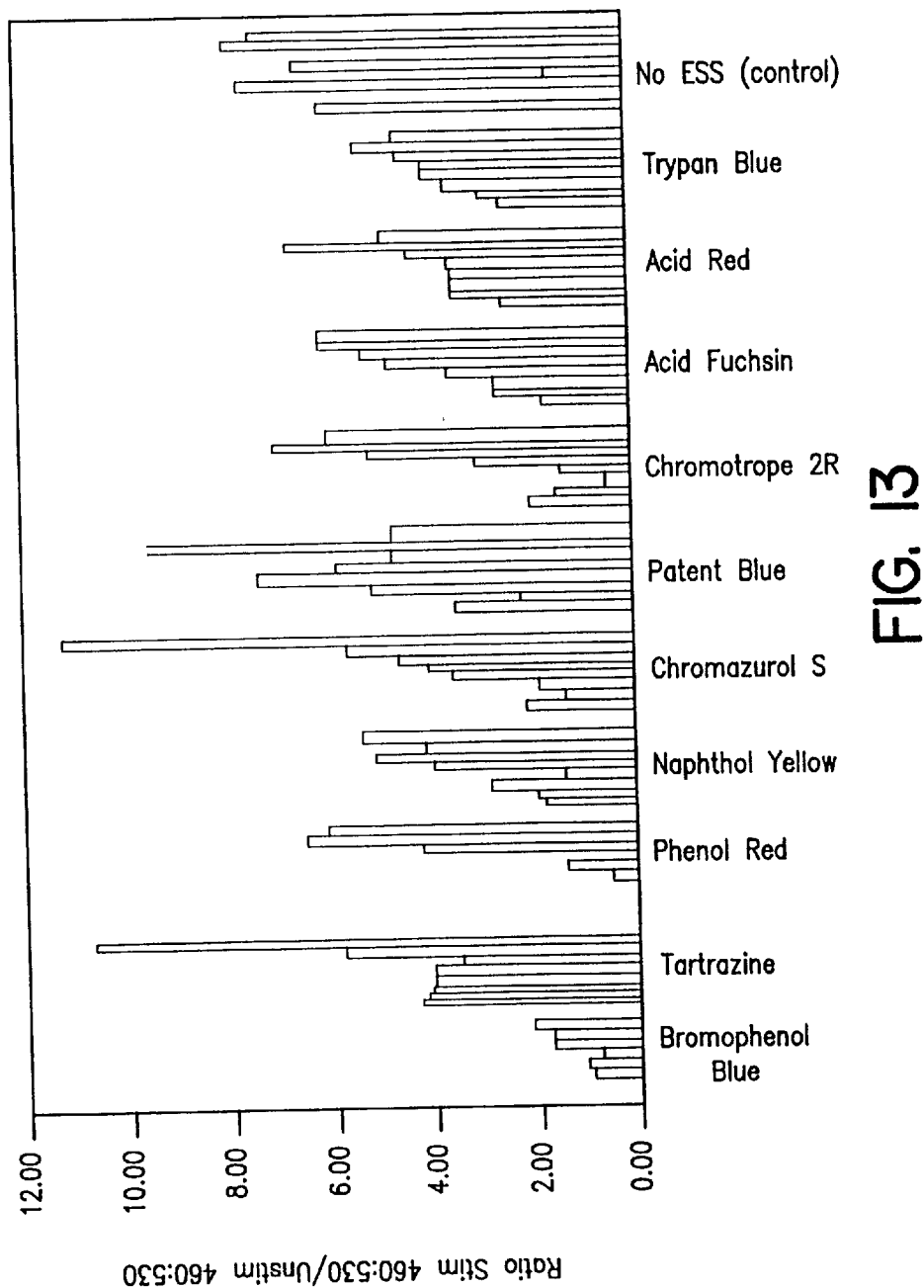
FIG. 13 shows the ability of cells treated with photon reducing agents to express beta-lactamase after stimulation with an appropriate agonist.

FIG. 13 illustrates the ability of cells treated with candidate dye-based photon reducing agents to express beta-lactamase upon stimulation with agonist, load substrate and convert substrate. Direct observation of the cells also showed that the cells loaded substrate to its trapped form, as well as having beta-lactamase activity. 2-fold dilutions of ESS dyes ranging from final concentrations of 0.039 mM (left) to 10 mM (right), with the exception of Patent Blue, which ranged from 0.022 mM (left) to 2.75 mM (right). Data is presented as a ratio of ratios ([agonist stimulated cells at emission wavelengths 460/530 nm]/[unstimulated cells emission 460/530 nm]).

These results demonstrate that cells treated with candidate dye-based photon reducing agents can load and convert substrate to its trapped form and support G-protein coupled receptor activation and reporter gene expression. Substrate loading and trapping indicates that the cell membrane is intact during candidate photon reducing agent treatment. Substrate trapping also indicates that intracellular esterases are sufficiently active to convert CCF2/AM into its trapped form CCF2. G-protein coupled receptor activation, gene activation and gene transcription processes also remain active in the presence of candidate photon reducing agents, as evidenced by beta-lactamase expression. Finally, beta-lactamase activity is sufficiently high in cells treated with candidate photon reducing agents to permit signal detection comparable to signal detection in the absence of candidate photon reducing agents. In some instances, signal over background from beta-lactamase expressing cells were actually increased by the presence of candidate photon reducing agents, suggesting that combinations of photon reducing reagents can actually provide superior results.

These experiments are quite rigorous in the testing of candidate photon reducing agents because the length of incubation with such photon reducing agents was approximately three hours and the photon reducing agents were added prior to gene activation and expression. In many screening and assay protocols, photon reducing agents can be added just prior to fluorescence detection, thereby minimizing the effects such photon reducing agents may have on the cells or assay.

Example 10

Dye-Based Photon Reducing Agent Sets Reduce Undesired Fluorescence in Cell Based Assays Better than a Single Dye-Based Photon Reducing Agent To investigate the ability of dye-based photon reducing agent sets to reduce undesired fluorescence in a cell-based assay, dye-based photon reducing agent sets were compared with a single photon reducing agent in the cell-based assays described herein. Dye-based photon reducing agent sets refer to at least two dye-based photon reducing agents. The following experiments demonstrate that dye-based photon reducing agent sets can be yield better cell based assay results, such as improved signal to noise ratios and are more robust at protecting against undesired fluorescence.

The photon reducing agent considered for use in the sets were selected from a number of dyes based on the following criteria: solubility in aqueous solution, having sufficiently high molar extinction coefficient, having low toxicity to mammalian cells, and not interfering with gene expression, substrate loading, and substrate conversion. The following dyes were selected: Tartrazine, Naphthol Yellow, Chromotrope F8, Chromazurol S, Patent Blue, Chromotrope 2R, Acid Fuchsin, and Acid Red 37.

From this list of dyes, two mixtures were created, based on the absorbance spectra of the dyes. Dyes selection was based on which dye sets would absorb solution fluorescence over the range of wavelengths for CCF2 excitation, coumarin emission and fluorescein emission. The two mixtures were called "ESS Mix 1" and "ESS Mix 2." ESS Mix 1 was: 100 mM Tartrazine, 100 mM Chromotrope 2R, and 100 mM Acid Fuchsin. ESS Mix 2 was: 40 mM Tartrazine, 60 mM Acid Red 37, and 40 mM Acid Fuchsin.

The ESS dye mixtures were assayed for appropriate concentrations for optimal use in the homogeneous assay for beta-lactamase, as described herein. First, dilutions of ESS Mix 1 and ESS Mix 2 were tested using Red Food Dye as a control. In all cases tested, ESS Mix 1 and ESS Mix 2 improved the fluorescence readout more than Red Food Dye. Subsequent experiments were used to evaluate lower concentrations of the ESS mixtures in order to effectively titrate the amount of the ESS mixtures needed for optimal assay performance.

After the initial set of ESS mixture testing, one more variation of dyes was made. The third ESS mixture was given the name "Tararaf" (an acronym for Tartrazine, Acid Red 37 and Acid Fuchsin). Tararaf is: 50 mM Tartrazine, 60 mM Acid Red 37, 40 mM Acid Fuchsin.

Tararaf was compared to ESS Mix 1 and ESS Mix 2, as well as to the individual components of Tararaf and Red Food Dye, in cell-based assays using CCF2. Tararaf improved the fluorescence readout more than each of the individual components of the mixture did.

Figure 14A:
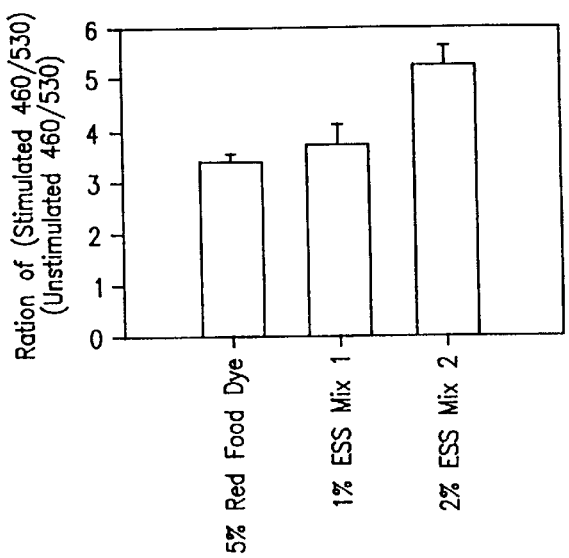
FIG. 14A and FIG. 14B show that photon reducing agent sets can reduce undesired fluorescence better than single dye-based photon reducing agents.
Figure 14B:
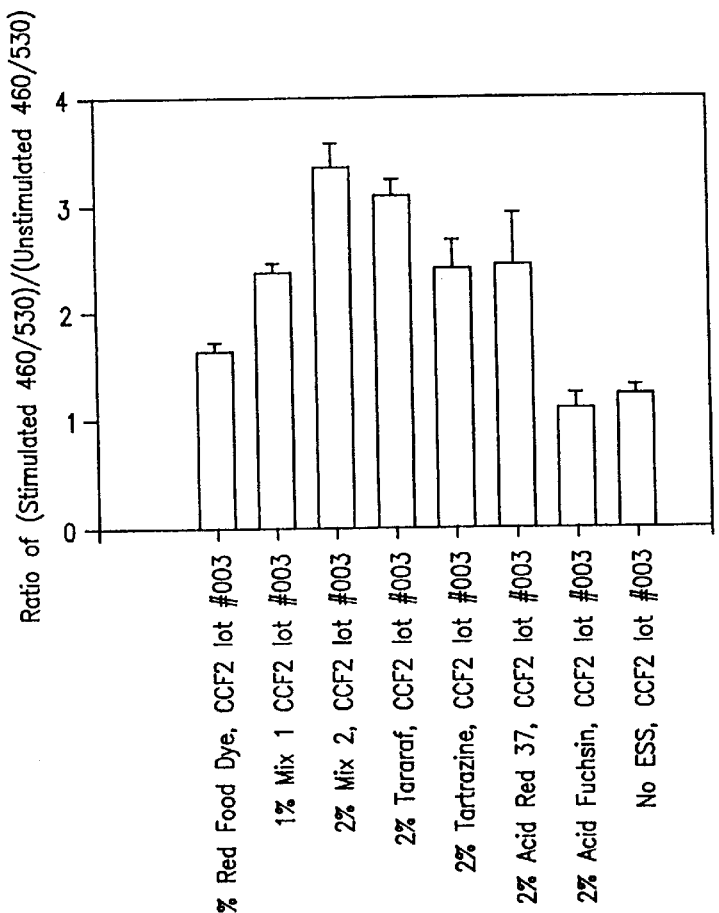

FIG. 14 shows the results of these experiments. These results demonstrate that photon reducing agent sets can improve signals from cell-based assays compared to either single photon reducing agents or no photon reducing agents.

Publications

All publications, including patent documents, world wide web sites and scientific articles, referred to in this application are incorporated by reference in their entirety for all purposes to the same extent as if each individual publication were individually incorporated by reference.

All headings are for the convenience of the reader and should not be used to limit the meaning of the text that follows the heading, unless so specified.

We claim:

1. A composition of matter, comprising:
   a) a membrane compartment in contact with a solid surface, wherein said membrane compartment comprises at least one photon producing agent, and
   b) an aqueous solution with at least one photon reducing agent, wherein said aqueous solution is in contact with an outer surface of said membrane compartment,
      wherein said at least one photon reducing agent is substantially impermeant to said membrane compartment,
      wherein said at least one photon reducing agent has an absorption spectrum that overlaps with the absorption, emission or excitation spectrum of said at least one photon producing agent, and
      wherein said at least one photon reducing agent is present in said aqueous solution at a concentration sufficient to reduce light emitted from said aqueous solution by at least 10% compared to the light emitted of said aqueous solution in the absence of said at least one photon reducing agent.

2. The composition of matter of claim 1, wherein said aqueous solution further comprises at least on photon producing agent.

3. The composition of matter of claim 2, wherein said at least one photon reducing agent is present in said aqueous solution at a concentration sufficient to reduce light emitted from said at least one photon producing agent present in said aqueous solution by at least 30% compared to the light emitted from said at least one photon producing agent in said aqueous solution in the absence of said at least one photon reducing agent.

4. The composition of matter of claim 2, wherein said aqueous solution further comprises a second photon producing agent that is a test chemical.

5. The composition of matter of claim 1, wherein said at least one photon reducing agent is present in said aqueous solution at a concentration that reduces undesired fluorescence from said aqueous solution by at least 40% compared to undesired fluorescence of said aqueous solution in the absence of said at least one photon reducing agent.

6. The composition of matter of claim 5, wherein said at least one photon reducing agent has solubility in water of about 100 mM or more.

7. The composition of matter of claim 1, wherein said at least one photon reducing agent has an absorption spectrum that overlaps with the emission or excitation spectrum of said at least one photon producing agent.

8. The composition of matter of claim 7, wherein said at least one photon reducing agent has an extinction coefficient of at least 10,000 $M^{-1}cm^{-1}$.

9. The composition of matter of claim 7, wherein said membrane compartment is a living cell.

10. The composition of matter of claim 9, wherein said at least one photon reducing agent is not acting as a pH indicator dye and said at least one photon reducing agent has an absorbance spectrum that overlaps with the emission or excitation spectrum of said at least one photon producing agent in said aqueous solution.

11. The composition of matter of claim 1, wherein said at least one photon producing agent in said aqueous solution exhibits transfer energy to said at least one photon reducing agent.

12. The composition of matter of claim 11, wherein said membrane compartment is a living cell and said at least one photon reducing agent is a dye.

13. The composition of matter of claim 12, wherein said living cell is a member of a plurality of living cells in a volume less than about 5 microliters.

14. The composition of matter of claim 12, wherein said composition further includes a microplate and said living cell is a member of a plurality of living cells in a well of said microplate.

15. The composition of matter of claim 14, wherein said microplate has 864 or greater wells.

16. The composition of matter of claim 1, wherein said at least one photon reducing agent has an extinction coefficient of at least 10,000 $M^{-1}cm^{-1}$ and is present at a concentration of at least about 0.1 mM.

17. The composition of matter of claim 1, wherein said composition further comprises a system to launch light of a predetermined wavelength through the bottom of an assay surface, wherein said predetermined wavelength is an excitation wavelength for said at least one photon producing agent.

18. The composition of matter of claim 1, wherein said at least one photon reducing agent is present in said aqueous solution at a concentration that reduces fluorescence from said aqueous solution by at least 75% compared to fluorescence of said aqueous solution in the absence of said at least one photon reducing agent.

19. The composition of matter of claim 1, wherein said least one photon reducing agent is non-toxic to said living cell over the time frame of the assay.

20. The composition of matter of claim 1, wherein said at least one photon reducing agent is present in said aqueous solution at a concentration sufficient to reduce light emission from said aqueous solution by between 70 and 99% compared to light emission of said aqueous solution in the absence of said at least one photon reducing agent.

21. The composition of matter of claim 1, wherein said at least one photon reducing agent is present in said aqueous solution at a concentration of between 0.1 mM and 10 mM.

22. The composition of matter of claim 1, wherein said at least one photon reducing agent is present in said aqueous solution at a concentration of between 0.5 mM and 5 mM.

23. The composition of matter of claim 1, wherein said aqueous solution comprises at least two photon reducing agents.

24. The composition of matter of claim 23, wherein one of said at least two photon reducing agents includes Tartrazine.

25. The composition of matter of claim 1, wherein said aqueous solution comprises at least three photon reducing agents.

26. The composition of matter of claim 1, wherein said at least one photon reducing agents includes Tartrazine.

27. The composition of matter of claim 1, wherein said at least one photon reducing agents includes chromotrope 2R.

28. The composition of matter of claim 1, wherein said at least one photon reducing agents includes Acid Fuchsin.

29. The composition of matter of claim 1, wherein said at least one photon reducing agents includes Patent Blue.

30. The composition of matter of claim 1, wherein said at least one photon reducing agents includes Acid Red 37.

31. The composition of matter of claim 1, wherein said at least one photon reducing agents includes chromotrope F8.

32. The composition of claim 1, wherein said at least one photon reducing agent has an intracellular concentration of less than 30% of the concentration of said at least one photon reducing agent outside of said membrane compartment.

33. The composition of claim 1, wherein said at least one photon reducing agent has an intracellular concentration of less than 10% of the concentration of said at least one photon reducing agent outside of said membrane compartment.

34. A composition of matter, comprising:
  a) at least one first photon producing agent internalized in a living cell in optical contact with a solid surface that can pass light of a predetermined wavelength that overlaps with the excitation spectrum of a second photon producing agent to excite said second photon producing agent, and
  b) at least one photon reducing agent in an aqueous solution surrounding said living cell,
    wherein said at least one photon reducing agent has an absorption spectra that overlaps with the absorption, emission or excitation spectra of said at least one first photon producing agent, and
    wherein said photon reducing agent is substantially impermeant to said membrane compartment, and
    wherein said at least one photon reducing agent is present in said aqueous solution at a concentration sufficient to reduce light emitted from said aqueous solution by at least 10% compared to the light emitted of said aqueous solution in the absence of said at least one photon reducing agent.

35. The composition of matter of claim 34, wherein said at least one photon reducing agent is present in said aqueous solution at a concentration that reduces fluorescence from said aqueous solution by at least 75% compared to fluorescence of said aqueous solution in the absence of said at least one photon reducing agent.

36. The composition of matter of claim 34, wherein said at least one photon reducing agent is present in said aqueous solution at a concentration of between 0.1 mM and 10 mM.

37. The composition of matter of claim 34, wherein said at least one photon reducing agent is present in said aqueous solution at a concentration of between 0.5 mM and 5 mM.

38. The composition of matter of claim 34, wherein said aqueous solution comprises at least two photon reducing agents.

39. The composition of matter of claim 38, wherein one of said at least two photon reducing agents includes Tartrazine.

40. The composition of matter of claim 34, wherein said aqueous solution comprises at least three photon reducing agents.

41. The composition of matter of claim 34, wherein said at least one photon reducing agents includes Tartrazine.

42. The composition of matter of claim 34, wherein said at least one photon reducing agents includes chromotrope 2R.

43. The composition of matter of claim 34, wherein said at least one photon reducing agents includes Acid Fuchsin.

44. The composition of matter of claim 34, wherein said at least one photon reducing agents includes Patent Blue.

45. The composition of matter of claim 34, wherein said at least one photon reducing agents includes Acid Red 37.

46. The composition of matter of claim 34, wherein said at least one photon reducing agents includes chromotrope F8.

47. The composition of claim 34, wherein said at least one photon reducing agent has an intracellular concentration of less than 30% of the concentration of said at least one photon reducing agent outside of said membrane compartment.

48. The composition of claim 34, wherein said at least one photon reducing agent has an intracellular concentration of less than 10% of the concentration of said at least one photon reducing agent outside of said membrane compartment.

* * * * *